United States Patent
Beight et al.

(10) Patent No.: US 6,916,840 B2
(45) Date of Patent: Jul. 12, 2005

(54) SPLA2 INHIBITORS

(75) Inventors: Douglas Wade Beight, Frankfort, IN (US); Michael Dean Kinnick, Indianapolis, IN (US); Ho-Shen Lin, Indianapolis, IN (US); John Michael Morin, Jr., Brownsburg, IN (US); Michael Enrico Richett, Indianapolis, IN (US); Daniel Jon Sall, Greenwood, IN (US); Jason Scott Sawyer, Indianapolis, IN (US); Edward C R Smith, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 70 days.

(21) Appl. No.: 10/450,860

(22) PCT Filed: Dec. 6, 2001

(86) PCT No.: PCT/US01/43182

§ 371 (c)(1),
(2), (4) Date: Jun. 16, 2003

(87) PCT Pub. No.: WO02/057231

PCT Pub. Date: Jul. 25, 2002

(65) Prior Publication Data

US 2004/0063967 A1 Apr. 1, 2004

Related U.S. Application Data

(63) Continuation of application No. 60/256,294, filed on Dec. 18, 2000.

(51) Int. Cl.$^7$ .................... A61K 31/40; C07D 209/56
(52) U.S. Cl. ...................................... 514/411; 548/427
(58) Field of Search ................... 548/427; 514/415, 514/411

(56) References Cited

FOREIGN PATENT DOCUMENTS

| EP | 0 620 215 | 10/1994 |
|---|---|---|
| EP | 0 675 110 | 10/1995 |
| WO | WO 00/37358 | 6/2000 |

Primary Examiner—Johann Richter
Assistant Examiner—Ebenezer Sackey
(74) Attorney, Agent, or Firm—Francis O. Ginah

(57) ABSTRACT

A novel class of benz[g]indole compounds is disclosed together with the use of such compounds for inhibiting sPLA2 mediated release of fatty acids for treatment of Inflammatory Diseases such as septic shock.

13 Claims, No Drawings

SPLA2 INHIBITORS

This application claims the benefit of Provisional Application No. 60/256,294, filed Dec. 18, 2000.

FIELD OF THE INVENTION

This invention relates to novel benz[g]indole compounds useful for Inflammatory Diseases.

BACKGROUND OF THE INVENTION

The structure and physical properties of human non-pancreatic secretory phospholipase $A_2$ (hereinafter called, "sPLA$_2$") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds, which inhibit sPLA$_2$ mediated release of fatty acids (e.g., arachidonic acid). Such compounds would be of value in the general treatment of conditions induced and/or maintained by overproduction of sPLA$_2$; such as sepsis or pain.

It is desirable to develop new compounds and treatments for sPLA$_2$ induced diseases.

SUMMARY OF THE INVENTION

The present invention relates to a compound of formula (I) and pharmaceutically acceptable salt, solvate or prodrug thereof, useful for the treatment or prevention of inflammatory diseases:

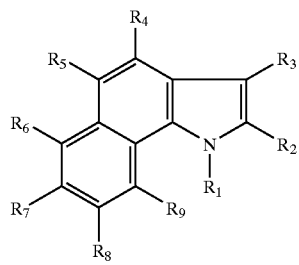

wherein;

$R_1$ is selected from group (a), (b), or (c) wherein;
(a) is $C_2$–$C_{20}$ alkyl, $C_2$–$C_{20}$ haloalkyl, $C_2$–$C_{20}$ alkenyl, $C_2$–$C_{20}$ alkynyl, carbocyclic radical, or heterocyclic radical, or
(b) is a member of (a) substituted with one or more independently selected non-interfering substituents;
(c) is the group -(L)-$R_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$ is hydrogen, or a group containing 1 to 10 non-hydrogen atoms plus any required hydrogen atoms;

$R_3$ is -($L_3$)-Z, where -($L_3$)- is a divalent linker group selected from a bond or a divalent group selected from:

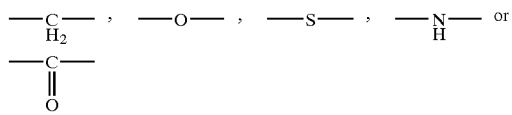

and Z is selected from an oxime amide or oxime thioamide group represented by the formulae,

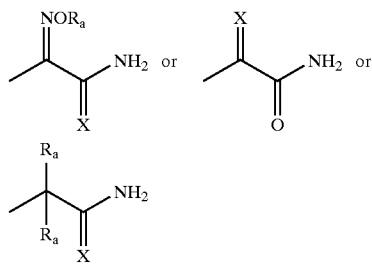

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, hydrogen, $CONH_2$, $CONHR^{4b}$ or —(La)-(acidic group) wherein -($L_a$)-, is an acid linker having an acid linker length of 1 to 8;
or the group -($L_h$)-(N-hydroxyfunctional amide group); wherein -($L_h$)-, is an N-hydroxyfunctional amide linker having a N-hydroxyfunctional amide linker length of 1 to 8; and wherein a N-hydroxyfunctional amide group is represented by the formula:

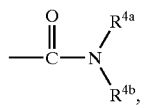

wherein $R^{4a}$ is selected from the group consisting of OH, ($C_1$–$C_6$)alkoxy, and aryloxy; and
wherein $R^{4b}$ is hydrogen or an organic substituent selected from the group consisting of ($C_1$–$C_8$)alkyl, aryl, ($C_7$–$C_{14}$) aralkyl, ($C_7$–$C_{14}$)alkaryl, ($C_3$–$C_8$)cycloalkyl, ($C_1$–$C_8$) alkoxyalkyl and these groups substituted with halogen, —$CF_3$, —OH, ($C_1$–$C_8$)alkyl, amino, carbonyl, and —CN;
or $R_4$ is the group -(Lc)- (acylamino acid group)- wherein the "acylamino acid group" is represented by the formula:

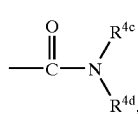

wherein $R^{4c}$ is selected from the group consisting of H, ($C_1$–$C_6$)alkyl, ($C_1$–$C_6$)alkoxy, heteroaryl and aryl, —$CF_3$; and wherein $NR^{4d}$ is an amino acid residue of either a natural or unnatural amino acid with the nitrogen atom being part of the amino group of the amino acid.

$R_5$ is selected from hydrogen, or a non-interfering substituent;

$R_6$, $R_7$, $R_8$, and $R_9$ are independently selected non-interfering substituents.

The present invention provides novel benz[g]indole compounds of formula I having potent and selective effectiveness as inhibitors of mammalian sPLA$_2$.

The present invention also relates to the use of novel benz[g]indole compounds of formula I useful in the treatment and/or prevention of Inflammatory Diseases.

This invention also relates to the use of a novel benz[g] indole compound of formula I to inhibit mammalian sPLA$_2$ mediated release of fatty acids.

The present invention provides a pharmaceutical composition containing any of the benz[g]indole compounds of the invention.

The present invention also relates to the use of a formulation comprising a compound of formula 1, and a carrier or diluent for the treatment or prevention of sepsis.

The present invention relates to the use of a pharmaceutical composition comprising a therapeutically effective amount of sPLA$_2$ inhibitor compounds of formula I and mixtures thereof for the manufacture of a medicament for the treatment of Inflammatory Diseases.

I. Definitions:

The terms, "mammal" and "mammalian" include human and domesticated quadrupeds. The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enteropathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

The term, "benz[g]indole", or "benz[g]indole nucleus" as used herein refers to a nucleus (having numbered positions) with the structural formula (X):

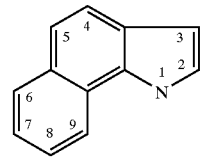

The benz[g]indole compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo. The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, benzyl, spiro[5.5]undecanyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, dibenzylyl and related dibenzylyl homologues represented by the formula (a):

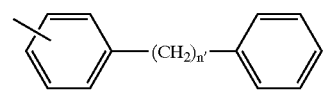

where n' is a number from 1 to 8.

The terms, "non-interfering substituent", or "non-interfering groups" refer to radicals suitable for substitution at positions 1, 2, 3, 4, 5, 6, 7, and/or 8 of the benz[g]indole nucleus and on other nucleus substituents (as hereinafter described for Formula I), and radicals suitable for substitution on the heterocyclic radical and carbocyclic radical as defined above. Illustrative non-interfering radicals are $(C_1-C_8)$alkyl, $(C_2-C_8)$alkenyl, $(C_2-C_8)$alkynyl, $(C_7-C_{12})$aralkyl, $(C_7-C_{12})$alkaryl, $(C_3-C_8)$cycloalkyl, $(C_3-C_8)$cycloalkenyl, phenyl, benzyl, toluyl, xylenyl, biphenyl, $(C_1-C_8)$alkoxy, $C_2-C_8$)alkenyloxy, $C_2-C_8$ alkynyloxy, $(C_2-C_{12})$ alkoxyalkyl, $(C_2-C_{12})$alkoxyalkyloxy, $C_2-C_{12}$ alkylcarbonyl, $(C_2-C_{12})$alkylcarbonylamino, $(C_2-C_{12})$alkoxyamino, $(C_2-C_{12})$alkoxyaminocarbonyl, $(C_1-C_{12})$alkylamino, $(C_1-C_6)$alkylthio, $(C_2-C_{12})$alkylthiocarbonyl, $(C_1-C_8)$alkylsulfinyl, $(C_1-C_8)$alkylsulfonyl, $(C_2-C_8)$haloalkoxy, $(C_2-C_8)$haloalkylsulfonyl, $(C_2-C_8)$haloalkyl, $(C_2-C_8)$hydroxyalkyl, —C(O)O(($C_2-C_8$)alkyl), —$(CH_2)_n$—O—($C_1-C_8$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and carbonyl; where n is from 1 to 8 and R is $(C_1-C_8)$alkyl.

The term, "organic substituent" refers to a monovalent radical consisting of carbon and hydrogen with or without oxygen, nitrogen, sulfur, halogen, or other elements. Illustrative organic substituents are $(C_1-C_8)$alkyl, aryl, $(C_7-C_{14})$aralkyl, $(C_7-C_{14})$alkaryl, $(C_3-C_8)$cycloalkyl, $(C_1-C_8)$alkoxyalkyl and these groups substituted with halogen, —$CF_3$, —OH, $(C_2-C_8)$alkyl, amino, carbonyl, and —CN.

The term "substituted group" is an organic group substituted with one or more non-interfering substituents.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the benz[g]indole nucleus have been drawn to show the first line as a connecting bond only. Thus, the group

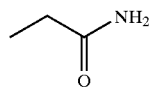

represents the acetamide radical or group, not the propanamide radical unless otherwise indicated.

The term, "N-hydroxyfunctional amide group" is represented by the formula:

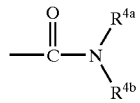

wherein $R^{4a}$ is selected from the group consisting of OH, $(C_1-C_6)$alkoxy, and aryloxy; and
wherein $R^{4b}$ is hydrogen or an organic substituent selected from the group consisting of $(C_1-C_8)$alkyl, aryl, $(C_7-C_{14})$aralkyl, $(C_7-C_{14})$alkaryl, $(C_3-C_8)$cycloalkyl, $(C_3-C_8)$alkoxyalkyl and these groups substituted with halogen, —$CF_3$, —OH, $(C_1-C_8)$alkyl, amino, carbonyl, and —CN.

The phrase, "N-hydroxyfunctional amide linker" refers to a divalent linking group symbolized as, -$(L_h)$-, which has the function of joining the 4-position of the benz[g]indole nucleus to an N-hydroxyfunctional amide group in the general relationship:

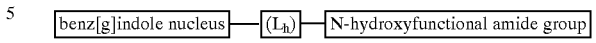

The words, "hydroxyfunctional amide linker length", refer to the number of atoms (excluding hydrogen) in the shortest chain of the linking group -$(L_h)$- that connects the 4-position of the benz[g]indole nucleus with the N-hydroxyfunctional amide group. The presence of a carbocyclic ring in -$(L_h)$- counts as the number of atoms approximately equivalent to the calculated diameter of the carbocyclic ring. Thus, a benzene or cyclohexane ring in the acid linker counts as 2 atoms in calculating the length of -$(L_h)$-. Illustrative "N-hydroxyfunctional amide linker" groups are;

(a)

(b)

(c)

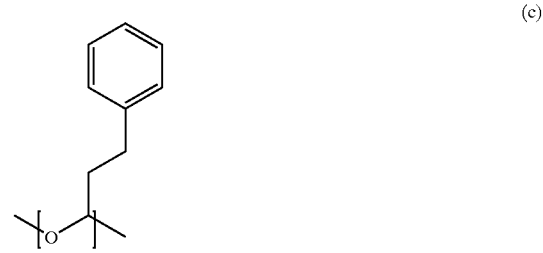

wherein, groups (a), (b) and (c) have acid linker lengths of 5, 7, and 2, respectively.

The term, "(acidic group)" means an organic group which when attached to a benz[g]indole nucleus at the 4-position, through suitable linking atoms (hereinafter defined as the "acid linker"), acts as a proton donor capable of hydrogen bonding. Illustrative of an (acidic group) are the following:

-5-tetrazolyl,

—$SO_3H$,

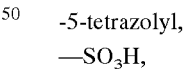

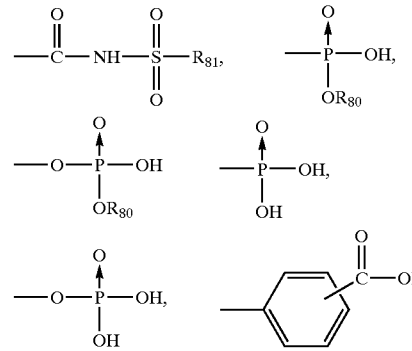

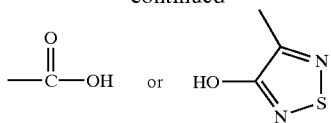

where n is 1 to 8, $R_{80}$ is a metal or $(C_1-C_8)$ and $R_{81}$ is an organic substituent or —$CF_3$.

The words, "acid linker" refer to a divalent linking group symbolized as, -$(L_a)$-, which has the function of joining the 4-position of the benz[g]indole nucleus to an acidic group in the general relationship:

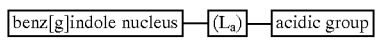

The words, "acid linker length", refer to the number of atoms (excluding hydrogen) in the shortest chain of the linking group -$(L_a)$- that connects the 4-position of the benz[g]indole nucleus with the acidic group. The presence of a carbocyclic ring in -$(L_a)$- counts as the number of atoms approximately equivalent to the calculated diameter of the carbocyclic ring. Thus, a benzene or cyclohexane ring in the acid linker counts as 2 atoms in calculating the length of -$(L_a)$-. Illustrative acid linker groups include;

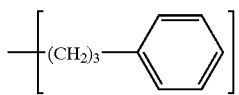

(a)

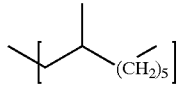

(b)

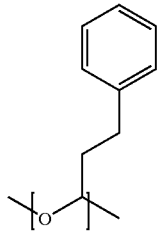

(c)

wherein, groups (a), (b), and (c) have acid linker lengths of 5, 7, and 2, respectively.

The term, "acylamino acid group" is represented by the formula:

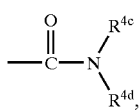

wherein $R^{4c}$ is selected from the group consisting of H, $(C_1-C_6)$alkyl, $(C_1-C_6)$alkoxy, heteroaryl and aryl, —$CF_3$; and wherein $NR^{4d}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof. Contemplated within the definition of amino acid are 1-proline, d-proline and derivatives thereof. Also contemplated within the definition of amino acids are peptides, polypeptides and derivatives thereof.

The term, "amino acid residue" refers to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

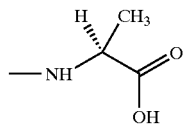

The words, "acylamino acid linker" refer to a divalent linking group symbolized as, -$(L_c)$-, which has the function of joining the 4-position of the benz[g]indole nucleus to an acylamino acid group in the general relationship:

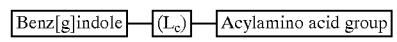

The words, "acylamino acid linker length", refer to the number of atoms (excluding hydrogen) in the shortest chain of the linking group -$(L_c)$- that connects the 4-position of the benz[g]indole nucleus with the acylamino acid group. The presence of a carbocyclic ring in -$(L_c)$- counts as the number of atoms approximately equivalent to the calculated diameter of the carbocyclic ring. Thus, a benzene or cyclohexane ring in the acid linker counts as 2 atoms in calculating the length of -$(L_c)$-. Illustrative "acylamino acid linker groups" include:

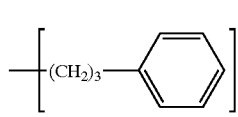

(a)

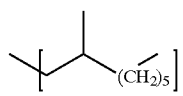

(b)

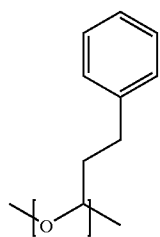

(c)

wherein, groups (a), (b) and (c) have acid linker lengths of 5, 7, and 2, respectively.

The term, "amine", includes primary, secondary and tertiary amines.

The term, "alkylene chain of 1 or 2 carbon atoms" refers to the divalent radicals, —$CH_2$—$CH_2$— and —$CH_2$—.

The term, "group containing 1 to 10 non-hydrogen atoms" refers to relatively small groups which form substituents at the 2-position of the benz[g]indole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —$CF_3$, —Cl, —Br, —$NO_2$, —CN, —SO₃; and (ii) groups having hydrogen atoms which contain less than 4 non-hydrogen atoms such as —CH₃, —C₂H₅, and —CH═CH₂.

The term "oxime amide" means the radical, —C(═NOR)—C(O)NH₂.

The term "thio-oxime amide" means the radical —C(═NOR)—C(S)—NH₂.

The term "spiro[5.5]undecanyl" refers to the group represented by the formula;

II. The benz[g]indole Compounds of the Invention:

The present invention provides a novel class of benz[g] indole compounds useful as sPLA₂ inhibitors for the treatment and/or prophylaxis of inflammation attendant to inflammatory diseases. Subclasses of benz[g]indole compounds of this invention include benz[g]indole oxyacid derivatives, benz[g]indole-3-oxime oxyacid derivatives, benz[g]indole-3-acetamide oxyacid derivatives, benz[g]indole-3-glyoxylamide-N-hydroxyfunctional amide derivatives, benz[g]indole-3-oxime amide-N-hydroxyfunctional amide derivatives, benz[g]indole-3-acetamide hydroxy functional amide derivatives, benz[g]indole-3-glyoxylamide acylamino acid derivatives, benz[g]indole-3-oxime amide acylamino acid derivatives, benz[g]indole-3-acetamide acylamino acid derivatives.

The compounds of the invention are represented by the general formula (I) and include a pharmaceutically acceptable salt, solvate or prodrug thereof;

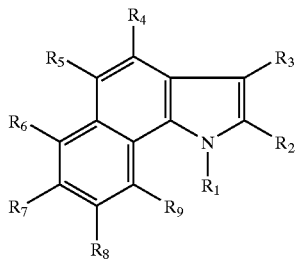

(I)

wherein;

R₁ is selected from group (a), (b), or (c) wherein;

(a) is C₂–C₂₀ alkyl, C₂–C₂₀ haloalkyl, C₂–C₂₀ alkenyl, C₂–C₂₀ alkynyl, carbocyclic radical, or heterocyclic radical, or (b) is a member of (a) substituted with one or more independently selected non-interfering substituents;

(c) is the group -(L)-R₈₀; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where R₈₀ is a group selected from (a) or (b);

R₂ is hydrogen, or a group containing 1 to 10 non-hydrogen atoms plus any required hydrogen atoms;

R₃ is -(L₃)-Z, where -(L₃)- is a divalent linker group selected from a bond or a divalent group selected from:

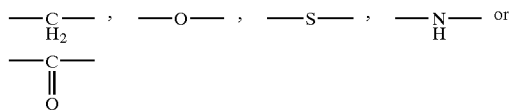

and Z is selected from an oxime amide or oxime thioamide group represented by the formulae,

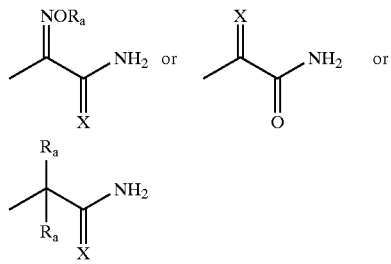

wherein X is oxygen or sulfur, R_a is independently selected from hydrogen, C₁–C₈ alkyl, aryl, C₁–C₈ alkaryl, C₁–C₈ alkoxy, aralkyl and —CN;

R₄ is the group, hydrogen, CONH₂, CONHR⁴ᵇ or —(La)-(acidic group) wherein -(L_a)-, is an acid linker having an acid linker length of 1 to 8;

or the group -(L_h)-(N-hydroxyfunctional amide group); wherein -(L_h)-, is an N-hydroxyfunctional amide linker having a N-hydroxyfunctional amide linker length of 1 to 8; and wherein a N-hydroxyfunctional amide group is represented by the formula:

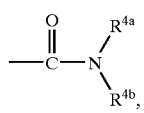

wherein R⁴ᵃ is selected from the group consisting of OH, (C₁–C₆)alkoxy, and aryloxy; and wherein R⁴ᵇ is hydrogen or an organic substituent selected from the group consisting of (C₁–C₈)alkyl, aryl, (C₇–C₁₄) aralkyl, (C₇–C₁₄)alkaryl, (C₃–C₈)cycloalkyl, (C₁–C₈) alkoxyalkyl and these groups substituted with halogen, —CF₃, —OH, (C₁–C₈)alkyl, amino, carbonyl, and —CN;

or R₄ is the group -(Lc)- (acylamino acid group)- wherein the "acylamino acid group" is represented by the formula:

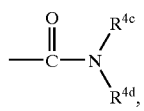

wherein R⁴ᶜ is selected from the group consisting of H, (C₁–C₆)alkyl, (C₁–C₆)alkoxy, heteroaryl and aryl, —CF₃; and wherein NR⁴ᵈ is an amino acid residue of either a natural or unnatural amino acid with the nitrogen atom being part of the amino group of the amino acid.

R₅ is selected from hydrogen, a non-interfering substituent; and

R₆, R₇, R₈, and R₉ are independently selected non-interfering substituents.

Preferred Subgroups of Compounds of Formula (I):
Preferred $R_1$ Substituents:

A preferred subclass of compounds of formula (I) are those where for $R_1$ the divalent linking group -($L_1$)- is a group represented by any one of the following formulae (Ia), (Ib), (Ic), (Id), (Ie), or (If):

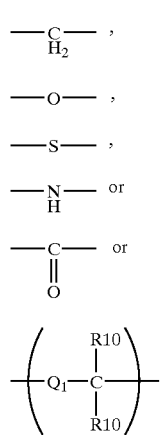

where $Q_1$ is a bond or any of the divalent groups (Ia), (Ib), (Ic), (Id), (Ie), and (If) and each $R_{10}$ is independently hydrogen, $(C_1-C_8)$alkyl, $(C_1-C_8)$haloalkyl or $(C_1-C_8)$ alkoxy.

Particularly preferred as the linking group -($L_1$)- of $R_1$ is an alkylene chain of 1 or 2 carbon atoms, namely, —($CH_2$)— or —($CH_2$—$CH_2$)—.

The preferred group for $R_{11a}$ is a substituted or unsubstituted group selected from the group consisting of $(C_5-C_{14})$ cycloalkyl, $(C_5-C_{14})$cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

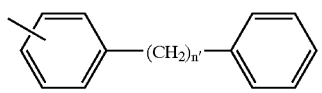

where n' is a number from 1 to 8.

Particularly preferred are compounds wherein for $R_1$ the combined group -($L_1$)-$R_{11a}$ is selected from the group consisting of

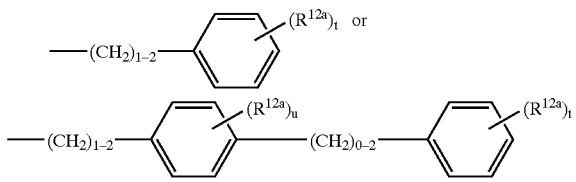

where $R^{12a}$ is a radical independently selected from halo, $(C_1-C_8)$alkyl, $(C_1-C_8)$alkoxy, —S—(($C_1-C_8)$alkyl), —o— (($C_1-C_8)$alkyl) and $(C_1-C_8)$haloalkyl where t is a number from 0 to 5 and u is a number from 0 to 4.

is the group -($L_1$)-$R_{11a}$; where, -($L_1$)- is a divalent linking group of 1 to 8 atoms and where $R_{11a}$ is a group selected from (a) or (b).

Preferred for $R_{11a}$ is —($CH_2$)m-$R^{12a}$ wherein m is an integer from 1 to 6, and $R^{12a}$ is (d) a group represented by the formula:

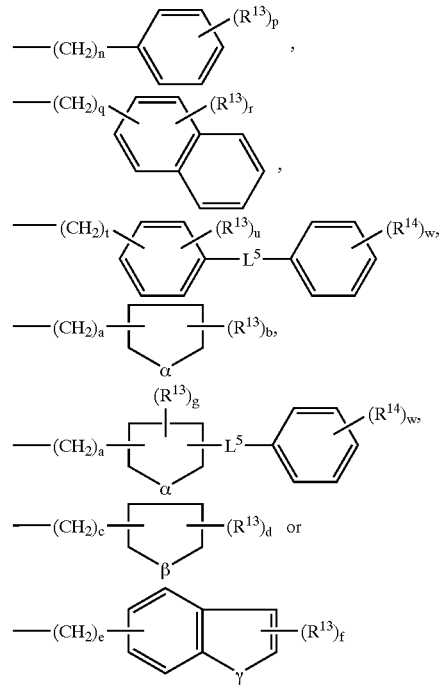

wherein a, c, e, n, q, and t are independently an integer from 0 to 2, $R^{13}$ and $R^{14}$ are independently selected from a halogen, $C_1$ to $C_8$ alkyl, $C_1$ to $C_8$ alkyloxy, $C_1$ to $C_8$ alkylthio, aryl, heteroaryl, and $C_1$ to $C_8$ haloalkyl, α is an oxygen atom or a sulfur atom, $L^5$ is a bond, —($CH_2$)v—, —C=C—, —CC—, —O—, or —S—, v is an integer from 0 to 2, β is —$CH_2$— or —($CH_2$)$_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

Preferred $R_2$ Substituents:

$R_2$ is preferably selected from the group consisting of hydrogen, $(C_1-C_4)$alkyl, $(C_2-C_4)$alkenyl, —O—(($C_1-C_4)$ alkyl), —S—(($C_1-C_3)$alkyl), —($C_3-C_4$)cycloalkyl, —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

Preferred $R_3$:

A preferred subgroups of $R_3$ is -($L_3$)-Z, where -($L_3$)- is a divalent linker group selected from a bond or a divalent group selected from:

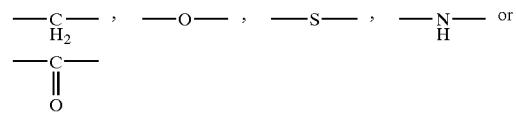

and Z is selected from a glyoxylamide, acetamide, an oxime amide or oxime thioamide group represented by the formulae,

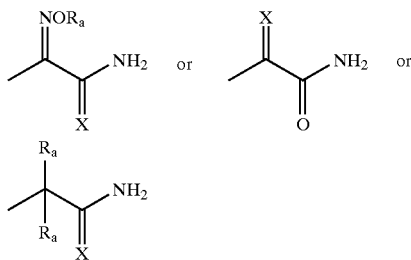

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

A more preferred subclass of compounds of formula (I) are those wherein X is oxygen.

Also more preferred is a subclass of compounds of formula I wherein Z is a glyoxylamide (glyoxamide) group represented by

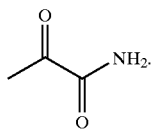

Another preferred subclass of compounds of formula (I) are those wherein Z is an amide group

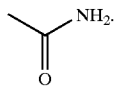

Also preferred are compounds of formula (I) wherein Z is an acetamide group represented by the formulae:

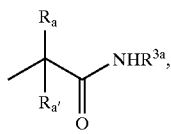

wherein $R_a$ and $R_{a'}$ are independently selected from hydrogen, $(C_1$–$C_8)$alkyl, aryl, $(C_1$–$C_8)$alkaryl, $(C_1$–$C_8)$ alkoxy, aralkyl and —CN, and $R^{3a}$ is hydrogen, $NH_2$, methyl, or ethyl.

For the group $R_3$ it is most preferred that the linking group -($L_3$)- be a bond.

Preferred R4 Substituents:

A preferred subgroup of $R_4$ is the group, hydrogen, $CONH_2$, $CONHR^{4b}$ or —(La)-(acidic group) wherein -($L_a$)-, is an acid linker having an acid linker length of 1 to 8;

or the group -($L_h$)-(N-hydroxyfunctional amide group); wherein -($L_h$)-, is an N-hydroxyfunctional amide linker having an N-hydroxyfunctional amide linker length of 1 to 8; and wherein a N-hydroxyfunctional amide group is represented by the formula:

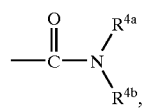

wherein $R^{4a}$ is selected from the group consisting of OH, $(C_1$–$C_6)$alkoxy, and aryloxy; and wherein $R^{4b}$ is hydrogen or an organic substituent selected from the group consisting of $(C_1$–$C_8)$alkyl, aryl, $(C_7$–$C_{14})$ aralkyl, $(C_7$–$C_{14})$alkaryl, $(C_3$–$C_8)$cycloalkyl, $(C_1$–$C_8)$ alkoxyalkyl and these groups substituted with halogen, —$CF_3$, —OH, $(C_1$–$C_8)$alkyl, amino, carbonyl, and —CN;

or $R_4$ is the group -(Lc)- (acylamino acid group)- wherein the "acylamino acid group" is represented by the formula:

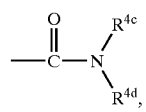

wherein $R^{4c}$ is selected from the group consisting of H, $(C_1$–$C_6)$alkyl, $(C_1$–$C_6)$alkoxy, heteroaryl and aryl, —$CF_3$; and wherein $NR^{4d}$ is an amino acid residue of either a natural or unnatural amino acid with the nitrogen atom being part of the amino group of the amino acid. A most preferred subgroup of $R_4$ is the group, hydrogen, $CONH_2$, $CONHR^{4b}$ or —(La)-(acidic group) wherein -($L_a$)-, is an acid linker having an acid linker length of 1 to 8;

Also preferred is a subclass of compounds of formula I wherein -($L_a$)- is an acid linker selected from the group consisting of;

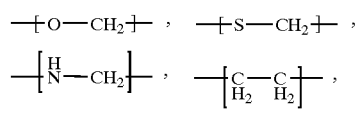

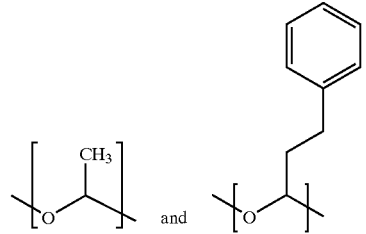

Another preferred subclass of compounds of formula I are those wherein $R_4$ is the group -(Lc)-(acylamino acid group)-, wherein -(Lc)- is an acylamino acid linker with an acylamino acid linker length of 2 or 3, and the "acylamino acid group" is represented by the formula:

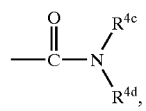

wherein R$^{4c}$ is selected from the group consisting of H, (C$_1$–C$_6$)alkyl, (C$_1$–C$_6$)alkoxy, heteroaryl and aryl, —CF$_3$; and wherein NR$^{4d}$ is an amino acid residue of either a natural or unnatural amino acid with the nitrogen atom being part of the amino group of the amino acid; and wherein the amino acid residue is derived from an amino acid selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof.

Another preferred subclass of compounds of formula (I) are those wherein R$_4$ is a substituent having an N-hydroxyfunctional amide linker with an N-hydroxyfunctional amide linker length of 2 or 3 and the N-hydroxyfunctional amide linker group, -(L$_h$)-, for R$_4$ is selected from a group represented by the formula;

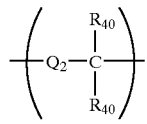

where Q$_2$ is selected from the group —(CH$_2$)—, —O—, —NH—, —C(O)—, and —S—, and each R$_{40}$ is independently selected from hydrogen, C$_1$–C$_8$ alkyl, aryl, C$_1$–C$_8$ alkaryl, C$_1$–C$_8$ alkoxy, aralkyl, and halo.

Most preferred subclasses of compound of formula (I) are compounds where the acid linker —(La)—, or the N-hydroxyfunctional amide linker, -(L$_h$)-, or the acylamino acid linker -(L$_c$)-, for R$_4$ is independently selected from the specific groups;

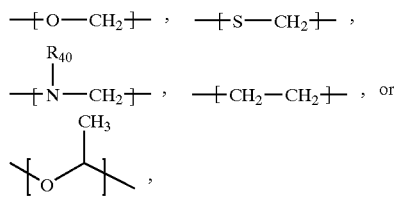

wherein R$_{40}$ is hydrogen or (C$_1$–C$_8$)alkyl.

Most preferred compounds of the invention are those having the general formula (II) or (III) or (IV) or a pharmaceutically acceptable salt, solvate or prodrug derivative thereof;

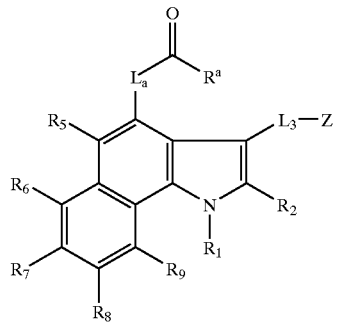

II

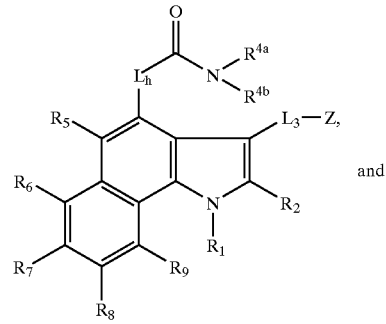

III and

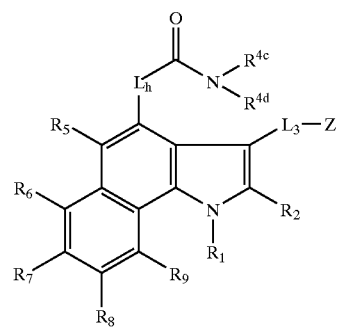

IV wherein;

R$^1$ is as described previously;

R$_2$ is as described previously;

R$_3$, R$_4$, R$_5$, R$_6$, R$_7$, R$_8$, and R$_1$ are as described previously;

L$_3$ is preferably a bond;

and Z is selected from an amide, thioamide or glyoxylamide, acetamide or thioacetamide, oxime, hydrazide radical (group) represented by the formulae,

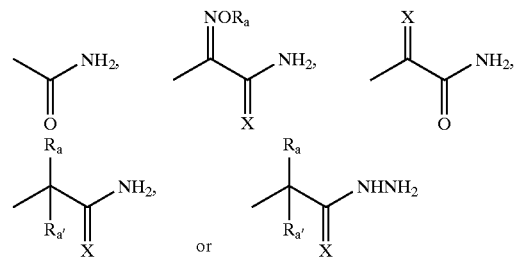

wherein X is oxygen or sulfur, R$_a$ and R$_{a'}$ are independently selected from hydrogen, (C$_1$–C$_8$)alkyl, aryl, and (C$_1$–C$_8$) alkaryl.

Preferred compounds of the invention are represented by the formulae (C1), (C2), (C3), (C4), (C5), or (C6):

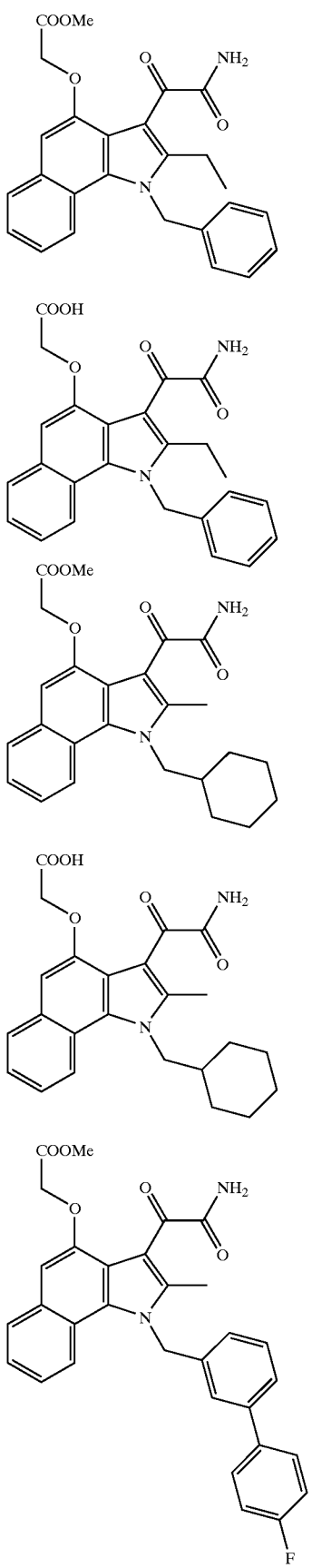

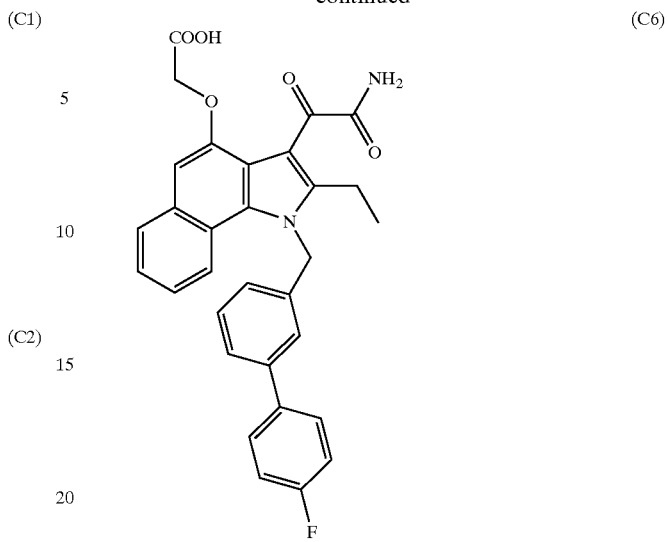

Most preferred compounds (and all pharmaceutically acceptable salts, solvates and prodrug derivatives thereof) which are illustrative of the compounds of the invention for treatment of a human afflicted with Inflammatory Disease, a pharmaceutically acceptable salt, solvate, or a prodrug derivative of a compound selected from the group consisting of:

2-[[3-(2-Amino-1,2-dioxoethyl)-2-ethyl-1-benzyl-1H-benz[g]indol-4-yl]oxy]acetic acid methyl ester hemihydrate;

2-[[3-(2-Amino-1,2-dioxoethyl)-2-ethyl-1-benzyl-1H-benz[g]indol-4-yl]oxy]acetic acid;

2-[[3-(2-amino-1, 2-dioxoethyl)-2-methyl-1-cyclohexylmethyl-1H-benz[g]indol-4-yl]oxy]acetic acid methyl ester;

2-[[3-(2-Amino-1,2-dioxoethyl)-2-methyl-1-cyclohexylmethyl-1H-benz[g]indol-4-yl]oxy]acetic acid;

2-[[3-(2-Amino-1,2-dioxoethyl)-2-methyl-1-[3-(4-fluorophenyl)benzyl]-1H-benz[g]indol-4-yl]oxy]acetic acid methyl ester; and 2-[[3-(2-Amino-1,2-dioxoethyl)-2-methyl-1-[3-(4-fluorophenyl)benzyl]-1H-benz[g]indol-4-yl]oxy]acetic acid.

The salts of the benz[g]indole compounds represented by formulae (I), (II), (III), and (IV) are an additional aspect of the invention.

In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25, 099–6).

Morpholinylethyl ester prodrugs may be prepared by reaction of the sodium salt of a compound of formula (I) (in a medium such as dimethylformamide) with 4-(2-chloroethyl)morpholine hydrochloride (available from Aldrich Chemical Co., Milwaukee, Wis. USA, Item No. C4, 220–3).

(III) Method of Preparing the benz[g]indole-3-glyoxylamide Compound:

The benz[g]indole-3-glyoxylamide compounds are compounds of this invention and are also useful as intermediates or starting materials for preparing other compounds of the invention. The benz[g]indole-3-glyoxylamide compounds are prepared by following a Scheme such as Scheme 1 shown below:

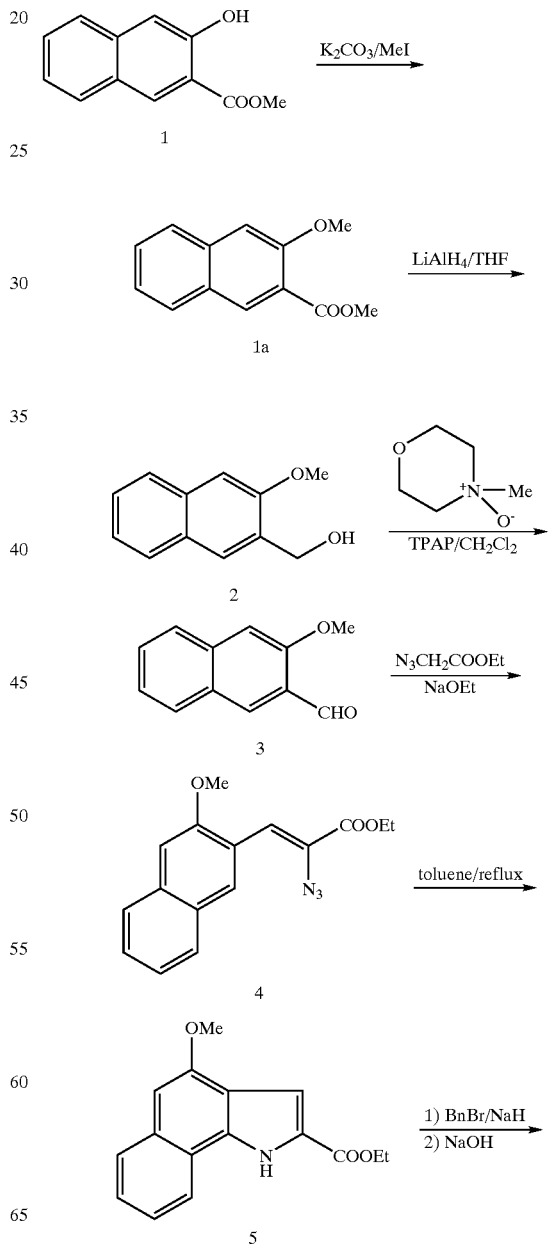

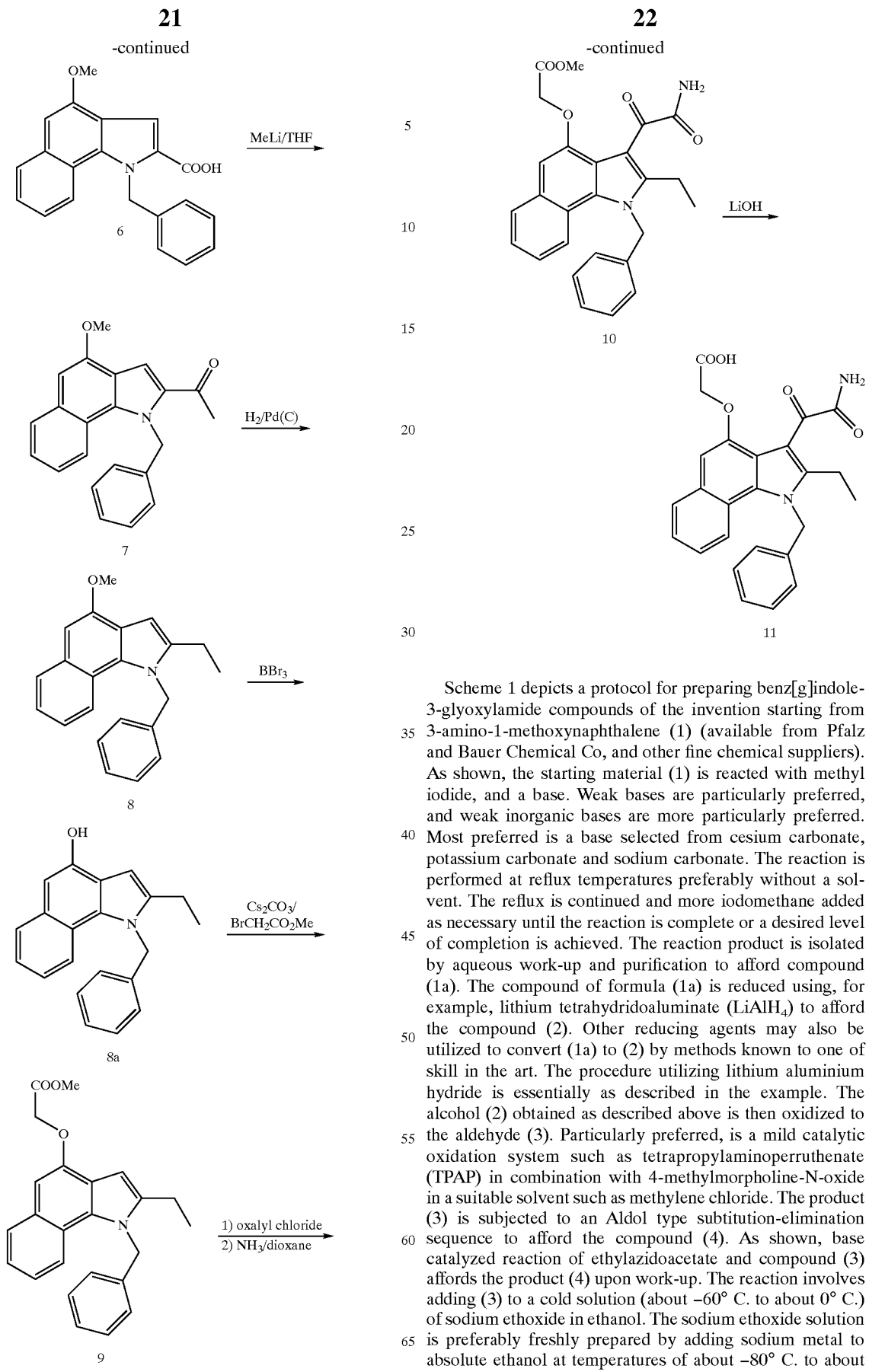

Scheme 1 depicts a protocol for preparing benz[g]indole-3-glyoxylamide compounds of the invention starting from 3-amino-1-methoxynaphthalene (1) (available from Pfalz and Bauer Chemical Co, and other fine chemical suppliers). As shown, the starting material (1) is reacted with methyl iodide, and a base. Weak bases are particularly preferred, and weak inorganic bases are more particularly preferred. Most preferred is a base selected from cesium carbonate, potassium carbonate and sodium carbonate. The reaction is performed at reflux temperatures preferably without a solvent. The reflux is continued and more iodomethane added as necessary until the reaction is complete or a desired level of completion is achieved. The reaction product is isolated by aqueous work-up and purification to afford compound (1a). The compound of formula (1a) is reduced using, for example, lithium tetrahydridoaluminate (LiAlH$_4$) to afford the compound (2). Other reducing agents may also be utilized to convert (1a) to (2) by methods known to one of skill in the art. The procedure utilizing lithium aluminium hydride is essentially as described in the example. The alcohol (2) obtained as described above is then oxidized to the aldehyde (3). Particularly preferred, is a mild catalytic oxidation system such as tetrapropylaminoperruthenate (TPAP) in combination with 4-methylmorpholine-N-oxide in a suitable solvent such as methylene chloride. The product (3) is subjected to an Aldol type subtitution-elimination sequence to afford the compound (4). As shown, base catalyzed reaction of ethylazidoacetate and compound (3) affords the product (4) upon work-up. The reaction involves adding (3) to a cold solution (about −60° C. to about 0° C.) of sodium ethoxide in ethanol. The sodium ethoxide solution is preferably freshly prepared by adding sodium metal to absolute ethanol at temperatures of about −80° C. to about −20° C. The product mixture is isolated from water as a solid, which may be recrystallized from hexane or other inert solvent. The product (4) is reductively cyclized by heating to reflux in toluene. After about 2–6 hours of heating at toluene reflux temperatures or when the reaction is deemed satisfactorily complete. The reaction mixture is allowed to cool to room temperature (about 21° C.). The resulting precipitate is filtered using an inert solvent, e.g., hexane as eluant to afford compound (5). The compound (5) is then substituted at the nitrogen with alkyl, aryl, alkylaryl groups or the like, to introduce the $R_1$ group, by a base catalyzed de-protonation followed by a nucleophilic attack on an electrophile. Electrophiles suitable for this reaction are those necessary to incorporate the $R_1$ group described previously and include for example, alkyl, aryl, and arylalkyl groups as the halides, sulfonates or other leaving groups. For example, the reaction of compound (5) with sodium hydride or a suitable base (i.e. n-BuLi, lithium diisopropyl amide) in a suitable solvent e.g., dimethylformamide, followed by addition of benzyl bromide for example, affords upon work-up the N-benzyl substituted derivative of compound (5). In a second step, the N-benzyl substituted derivative of compound (5) is hydrolyzed to the acid (6) using a base. A suitable base is an inorganic base. A preferred base is selected from the group consisting of sodium hydroxide, potassium hydroxide, lithium hydroxide and sodium bicarbonate. The compound of formula (6) is converted to the methylketone by reaction with methyllithium in a suitable solvent, e.g., tetrahydrofuran (THF). The reaction is effected by adding an excess (2–6 molar equivalents) of methyllithium to a solution of compound (6a). The reaction is performed at between about 0 to 40° C., preferably at about 20 to 30° C. Upon satisfactory completion (between 2 to 40 hours, typically between 5 to 20 hours), the reaction product (7) is isolated after an aqueous work-up as described in the examples. Next, the compound (7) is reduced to the compound (8). A preferred reducing agent for this reduction is hydrogen via hydrogenation using about 10% palladium-on-carbon catalyst in a suitable solvent or solvent mixture, preferably about a 1:1 solvent mixture of ethanol and ethyl acetate. The hydrogenation pressure is preferably less than about 45 psi (about 4 atm). The product (8) is isolated preferably by filtration followed by concentration of the filtrate.

The compound (8) is de-methylated by reaction with boron tribromide or sodium thioethoxide in a suitable solvent such as dichloromethane. About 1.0 to 2.0 equivalents of boron tribromide, for example, is typically sufficient to effect complete de-methylation. The de-methylation reaction temperature is from about −12° C. to about 10° C. Work-up is effected by stirring with methyl alcohol or other suitable protic solvent. The stirring in methyl alcohol, for example, is followed by neutralization with a base e.g., sodium bicarbonate. This is followed by extraction and purification of the organic phase by methods known to one of skill in the art to afford an intermediate product (8a). This intermediate may be isolated if desired or used in the next step directly. The product (8a) is dissolved in N,N-dimethylformamide or other suitable solvent i.e. THF, followed by addition of a slight excess (about 1. to 1.5 mole equivalents based on (8)) of cesium carbonate or other mild base, and methylbromoacetate to afford compound (9). Compound (9) is obtained after about 1 to 30 hours, preferably about 1 to 6 hours of reaction at about room temperature. Compound (9) is preferably isolated by aqueous extraction followed by chromatography.

The compound of formula (9) may be reacted with oxalyl chloride in a suitable solvent, e.g., methylene chloride at about 0 to 10° C. for about 1 to 4 hours, preferably, about 1–2 hours. This is followed by reaction with ammonia (THF solution saturated with ammonia) to afford the compound of formula (10).

The free acid (11) is optionally obtained by acidifying the saponifacation product of (10) or other basification reaction product, e.g. with potassium or lithium hydroxide. Most strong inorganic acids are suitable for acidification as described previously. However, the use of dilute HCl is preferred. The free acid (11) may be extracted into an organic phase if soluble, and dried by common laboratory methods or dried by removing water from the aqueous phase. Alternatively the saponification reaction (sodium hydroxide reaction with (10)) product, itself a compound of the invention may be isolated.

Conversion of the 3-glyoxylamide intermediate to the acylamino acid group or the N-hydroxyfunctional amide group derivative at 4-position is shown for example in Scheme 1a below:

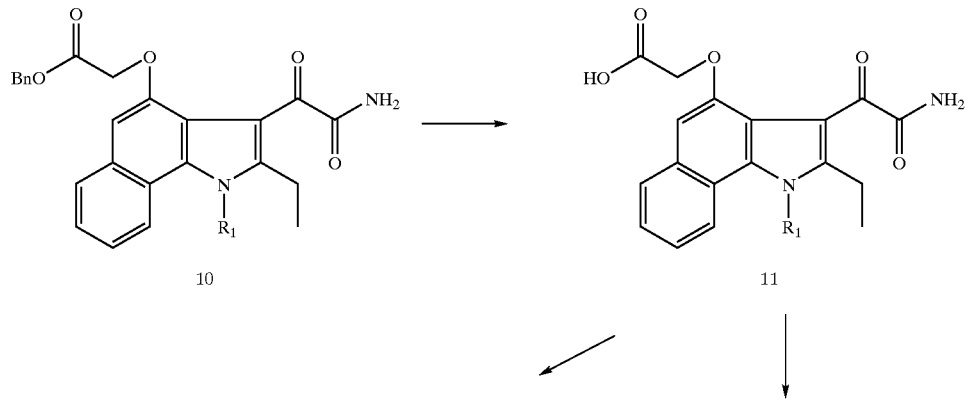

Scheme 1a

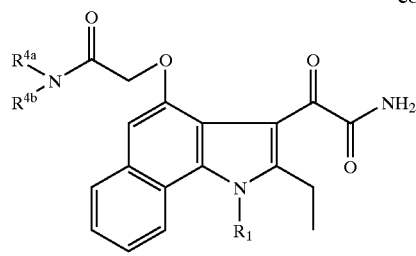 13

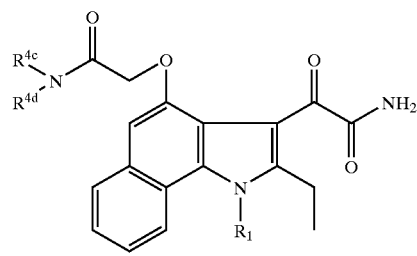 12

According to Scheme 1a, the oxyacetic acid ester (10) may be converted to the free acid (11) or to derivatives such as the ester or amide by procedures known to one of skill in the art or found in general reference texts. See for example, J. March *Advanced Organic Chemistry*, Wiley Interscience publishers, New York, N.Y., 1985, and R. C. Larock *Comprehensive Organic Transformations*, VCH Publishers, New York, N.Y., 1989.

The acid (11) is functionalized at the 4-position to the acylamino acid derivative (12) by room temperature base catalyzed condensation with an amino acid protected at the acid terminus (using a protecting group known in the literature but preferably the methyl ester). The reaction is accomplished using coupling agents such as HOBT/EDCI, BOP/collidine or other amide bond forming coupling agents.

The N-hydroxyfunctional amide group may be introduced via the acid (11) or acid salt thereof, by reaction with for example hydroxylamine hydrochloride or substituted hydroxylamine hydrochloride to afford the N-hydroxyfunctional amide compound of formula (13). For example, the acid compound (11) is reacted with o-(tert-butyldimethylsilyl) hydroxylamine at ambient temperature, in the presence of excess 2,4,6-collidine (collidine) and benzotriazol-1-yl-oxytris(dimethylamino)phosphonium hexafluorophosphonate (coupling catalyst, see *Tetrahedron Lett.*, 1219 (1975)) to afford after about 1–10 hours, the o-(tert-butyldimethylsilyl) substituted N-hydroxyfunctional amide derivative (not shown). The silyl or other protecting group is removed by well known methods such as, for example, the use of trifluoroacetic acid for removal of silyl protecting groups) to afford, for example, the N-hydroxyfunctional amide compound (13) wherein $R^{4a}$ is hydroxy and $R^{4b}$ is hydrogen.

Typically, the condensation or coupling is performed in a solvent such a dimethylformamide, tetrahydrofuran or aqueous mixtures of the like. In general protic solvents are preferred for the purpose of this invention. A base including for example, weak organic or inorganic bases catalyzes the reaction. Organic bases such as collidine are preferred. The reaction is also preferably run in the presence of agents that retard or reduce racemization of the hydroxyfunctional amide, the substituted hydroxylamine or its derivative. A particularly preferred agent is benzotriazolyl-N-oxy-tris (dimethylamino)phosphonium hexafluorophosphate. Upon completion of the reaction, the mixture is concentrated in vacuo. The resulting product mixture is chromatographed or crystallized, e.g., by sonication to obtain the target compound.

Benz[g]indol-3-acetamide $sPLA_2$ inhibitor derivatives of compounds (8) may be obtained by lithiation of compound (8) at the 3-position with an organolithium reagent e.g. n-butyllithium, followed by quenching the lithiated intermediate with ethylene oxide for example, to afford upon hydrolysis, the terminal alcohol derivative (14) as shown below in Scheme 2.

Scheme 2

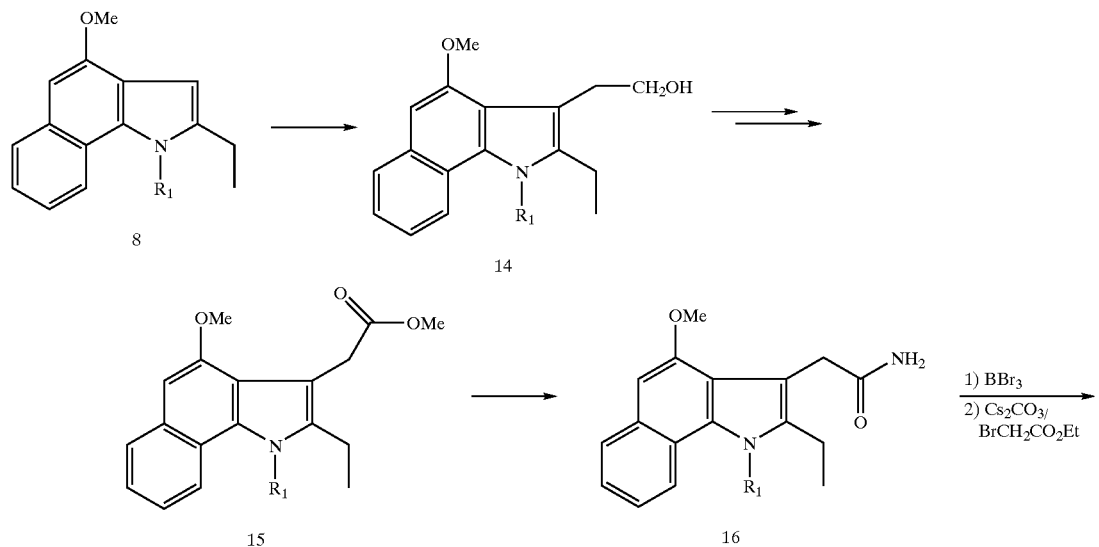

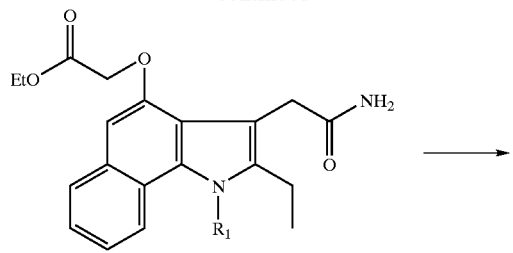

17

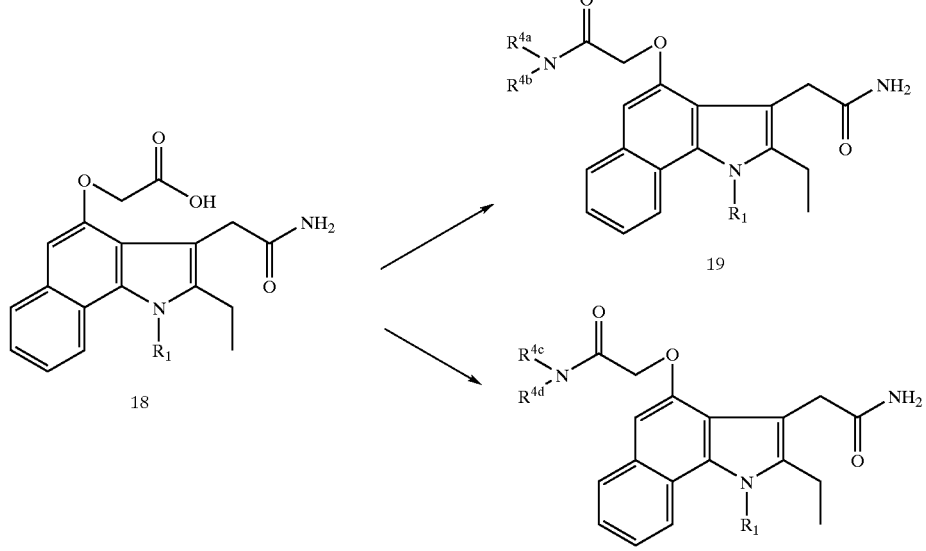

18

19

20

The resulting alcohol intermediate (14), itself a compound of the invention, may be converted by oxidation to the acid and further converted to the ester (15). Conversion of the alcohol intermediate (14) to an ester via an intermediate acid may be accomplished by oxidation of the alcohol with, for example, sodium hypochlorite in buffered t-butanol, followed by esterification of the incipient acid to the ester (15). Methods for these conversions are known to one of skill in the art and may be found in general reference texts disclosed previously. The ester (15) may be converted to the acetamide derivative (16) or other substituted acetamide compound. For example the reaction of the methyl acetate (15) with methylchloroaluminum amide in benzene or other suitable solvent or solvent mixtures affords the acetamide (compound 16). (See Levin, J. I.; Turos, E.; Weinreb, S. M. *An alternative procedure for the aluminum-mediated conversion of esters to amides. Syn. Comm.*, 1982, 12, 989–993).

Similarly, use of N-substituted methylchloroaluminum amides result in the corresponding substituted acetamides (see Weinreb supra). Alternatively the terminal alcohol (15) could be converted to the acyl halide (i.e. acyl chloride) via the acid oxidation product. The acid halide is then ammoniated to form the acetamide or substituted acetamide depending on amine used.

The 3-substituted benz[g]indole acetamide compounds described above may be converted to the corresponding 4-substituted N-hydroxyfunctional amide compounds (19) or the 4-substituted acylamino acid compounds (20) as described previously for the glyoxylamide compounds (Scheme 1a). For example, the methoxy group at the 4-position of compound (16) may be de-methylated as described above, reacted with bromomethylacetate and cesium bromide in DMF to form the oxyacetic acid ester group at the 4-position (compound 17). The oxyacetic acid ester group of (17) is further elaborated to the acid (18). The acid (18) is converted to the N-hydroxyfuntional amide group or the N-acylamino acid group as discussed above.

The substituted benz[g]indol-3-oxime amide compounds of the invention can be prepared following protocol of Scheme (3) below:

Scheme 3

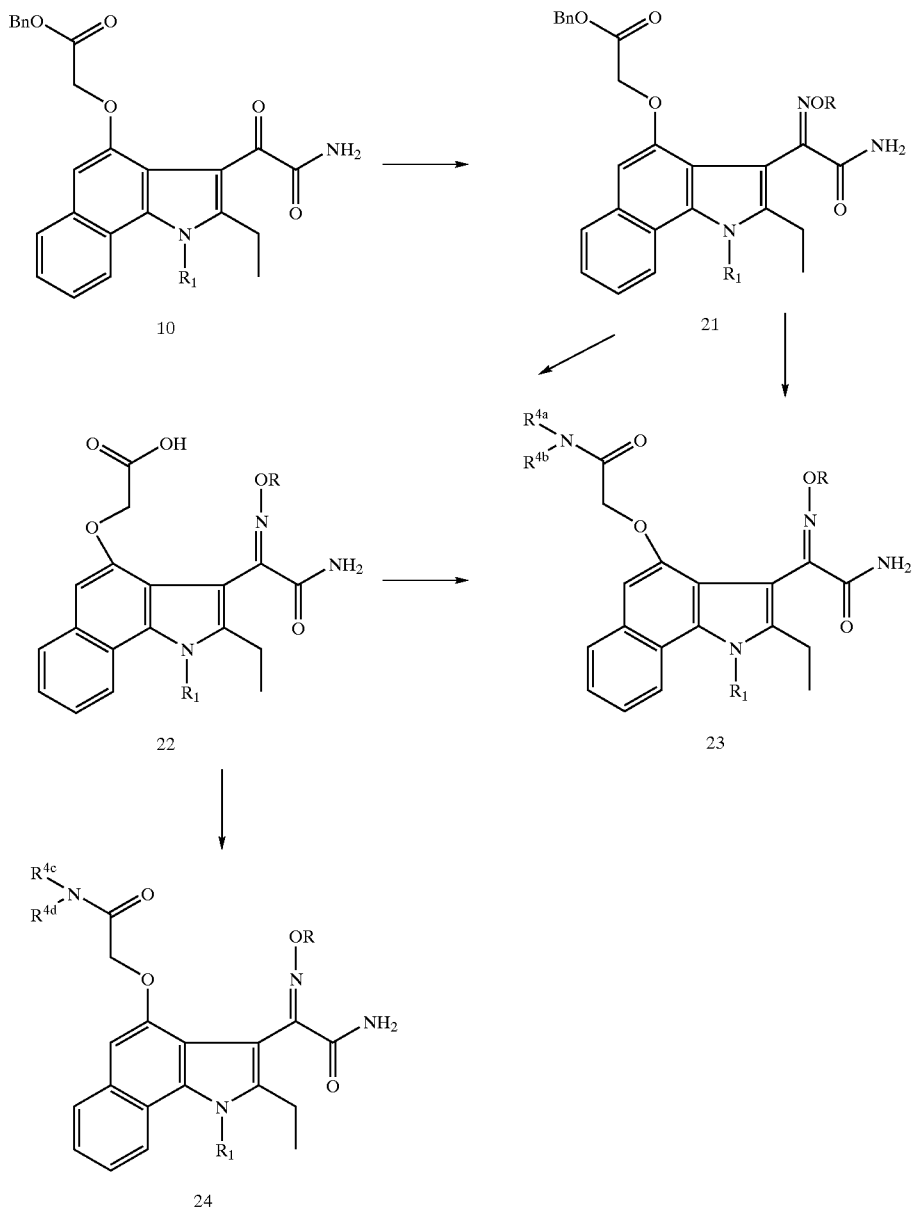

To introduce the oxime functionality, the compound of formula (10), for example, is heated with hydroxylamine hydrochloride (when R is H) in a THF/methanol mixture for about 1 to 8 hours or until the reaction is deemed satisfactorily complete. The reaction product compound (21), a compound of the invention, is isolated by chromatography or other known laboratory procedure. Substituted oximes such as when R is methyl, ethyl, phenyl or other non-interfering substituent may be prepared by reaction of the corresponding substituted hydroxylamine hydrochloride or free base with the glyoxylamide (e.g. compound (10)) as described supra.

Similarly, the ester i.e. methylester of the acid compound (11), or the acid salts thereof, may be converted to the corresponding oxime or substituted oxime functionality at the 3-position by the method described above. The ester functionality at the 4-position on the substituted benz[g] indole nucleus, as in for example, compound (21), may be converted to the acid by hydrolysis using lithium hydroxide or other known ester hydrolysis methods to afford a compound of formula (22). See, for example, J. March *Advanced Organic Chemistry*, Wiley Interscience publishers, New York, N.Y., 1985, and R. C. Larock *Comprehensive Organic Transformations*, VCH Publishers, New York, N.Y., 1989.

Furthermore, the oxime compounds prepared as described above may be converted to the N-hydroxyfunctional amide at the 4-position, via the ester (21), the free acid (22), or the acid salt functionalities at the 4-position. For example, Scheme (3) shows the conversion of the free acid compound (22) to the N-hydroxyfunctional amide compound (23).

Likewise, the compound (22) and analogs thereof may be converted to the acylamino acid compound (24) and corresponding homologs thereof, by procedures described supra.

IV. Methods of Using the Compounds of the Invention:

The benz[g]indole compounds described herein are believed to achieve their beneficial therapeutic action principally by direct inhibition of mammalian (including human) sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting mammalian sPLA$_2$ with a therapeutically effective amount of benz[g]indole compounds corresponding to Formulae (I) or (II) or (III) or (IV) as described herein including a combination thereof, a salt or a prodrug derivative thereof.

Another aspect of this invention relates to a method for treating Inflammatory Diseases such as inflammatory bowel disease, septic shock, adult respiratory distress syndrome, pancreatitis, trauma, asthma, bronchial asthma, allergic rhinitis, rheumatoid arthritis, osteoarthritis, and related diseases which comprises administering to a mammal (including a human) a therapeutically effective dose of a benz[g]indole compound of the invention.

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effect will, of course, be determined by the particular circumstances surrounding the case, including, for example, the compound administered, the route of administration and the condition being treated. Typical daily doses will contain a non-toxic dosage-level of from about 0.01 mg/kg to about 50 mg/kg of body weight of an active compound of this invention.

Preferably compounds of the invention per Formula (I) or (II) or (III) or (IV) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the benz[g]indole compound of the invention together with a pharmaceutically acceptable carrier or diluent therefor. The present pharmaceutical formulations are prepared by known procedures using well-known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. A preferred tablet formulation for oral administration is one that affords rapid dissolution in the mouth of a patient in need thereof.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methylcellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or (II) or (III) or (IV) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

| | Quantity (mg/tablet) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

| | Weight |
|---|---|
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| | |
|---|---|
| Active ingredient | 225 mg |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:

REACTION BUFFER -

| | |
|---|---|
| $CaCl_2.2H_2O$ | (1.47 g/L) |
| KCl | (7.455 g/L) |
| Bovine Serum Albumin (fatty acid free) (Sigma A-7030, product of Sigma Chemical Co., St. Louis MO, USA) | (1 g/L) |
| TRIS HCl pH 7.5 (adjust with NaOH) | (3.94 g/L) |

ENZYME BUFFER -

0.05 $NaOAc.3H_2O$, pH 4.5
0.2 NaCl
Adjust pH to 4.5 with acetic acid

DTNB -

5,5'-dithiobis-2-nitrobenzoic acid

RACEMIC DIHEPTANOYL THIO - PC racemic 1,2-bis(heptanoylthio)-1,2-dideoxy-sn-glycero-3-phosphorylcholine
TRITON X-100 ™ prepare at 6.249 mg/ml in reaction buffer to equal 10 uM.

Reaction Mixture

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

Tests were done in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were re-assayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus inhibition values in the range from 10–90% inhibition.

Results

| Compound of Example # | $IC_{50}$ ($\mu$M) (micromolar) |
|---|---|
| 1 | 0.048 |
| 2 | 0.010 |
| 3 | 0.148 |
| 4 | 0.011 |
| 5 | 0.176 |
| 6 | 0.021 |

While the present invention has been illustrated above by certain specific embodiments, it is not intended that these specific examples should limit the scope of the invention as described in the appended claims.

Experimental

All of the products of the Examples described below as well as intermediates used in the following procedures showed satisfactory NMR and IR spectra. They also had the correct mass spectral values.

EXAMPLE 1

2-[[3-(2-Amino-1,2-dioxoethyl)-2-ethyl-1-benzyl-1H-benz[g]indol-4-yl]oxy]acetic acid methyl ester hemihydrate

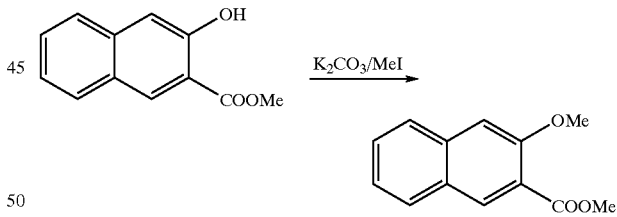

A. Preparation of 2-carbomethoxy-3-methoxynaphthalene. A mixture of 2-carbomethoxy-3-hydroxynaphthalene (72.0 g, 0.356 mol), cesium carbonate (138 g, 0.713 mol), and iodomethane (126 g, 0.890 mol) was refluxed for 24 h. An additional portion of iodomethane (80.0 g, 0.565 mol) was added and the mixture refluxed for 8 h then stirred at room temperature for 56 h. The mixture was diluted with water and extracted with diethyl ether. The organic layer was dried (sodium sulfate), filtered, and concentrated in vacuo to provide 70 g (91%) of the title product as an amber oil.

$^1$H NMR (CDCl$_3$) δ8.30 (s, 1H), 7.82 (d, J=7 Hz, 1H), 7.74 (d, J=7 Hz, 1H), 7.50 (t, J=7 Hz, 1H), 7.37 (t, J=7 Hz, 1H), 7.20 (s, 1H), 3.98 (s, 3H), 3.95 (s, 3H).

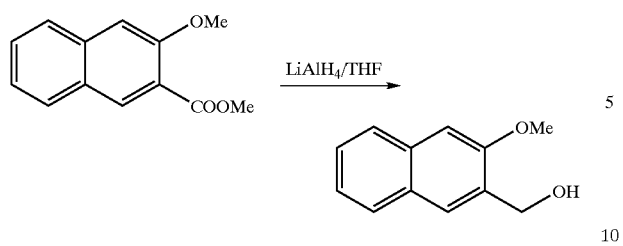

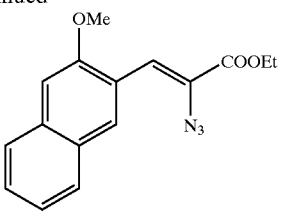

B. Preparation of 2-hydroxymethyl-3-methoxynaphthalene. To a suspension of lithium aluminum hydride (13.5 g, 0.356 mol) in tetrahydrofuran (300 mL) cooled to 0° C. was added a solution of 2-carbomethoxy-3-methoxynaphthalene (70.0 g, 0.324 mol) in tetrahydrofuran (150 mL) dropwise over 30 min. The mixture was stirred at room temperature for 3 h, diluted with hexane, and the reaction carefully quenched with 5 N aqueous sodium hydroxide solution (13 mL). The resulting mixture was stirred for 2 h then filtered. The filtrate was dried (sodium sulfate), filtered, and concentrated in vacuo to provide 56.8 g (93%) of the title compound as a thick amber oil. $^1$H NMR (CDCl$_3$) δ7.73 (m, 3H), 7.46 (t, J=6.7 Hz, 1H), 7.36 (t, J=7.8 Hz, 1H), 7.12 (s, 1H), 4.83 (s, 2H), 3.94 (s, 3H), 2.56 (s, 1H, —OH).

D. Preparation of 3-(3-methoxynaphth-2-yl)-2-azido-2-propenoic acid ethyl ester. To a solution of sodium (3.1 g, 0.14 mol) in absolute ethanol (300 mL) cooled to −20° C. was added a solution of 3-methoxy-2-naphthaldehyde (22.6 g, 0.121 mol) and ethyl azidoacetate (43.0 g, 0.333 mol) in ether in such a manner that the temperature of the reaction was maintained under −20° C. The mixture was carefully warmed to 10° C. where gas evolution was observed. The mixture was stirred for 4 h at a temperature of less than 20° C. The mixture was allowed to warm to room temperature and stirred for 18 h. The mixture was poured into water (1000 mL) resulting in a yellow precipitate. Collection via vacuum filtration provided 27.1 g (75%) of the title product (stereochemistry unknown), that may be recrystallized from hexane: mp 95–97° C. (dec). $^1$H NMR (CDCl$_3$) δ8.68 (s, 1 H), 7.80 (d, J=8 Hz, 1H), 7.69 (d, J=8 Hz, 1 H), 7.42 (t, J=7 Hz, 1H), 7.35 (t, J=7 Hz, 1H), 7.10 (s, 1H), 4.39 (q, J=7 Hz, 2H), 3.95 (s, 3H), 1.40 (t, J=7 Hz, 3H); MS FD+ m/e 297 (p).

Anal. Calcd for C$_{16}$H$_{15}$N$_3$O$_3$: C, 64.64; H, 5.09; N, 14.13. Found: C, 64.75; H, 5.24; N, 14.05.

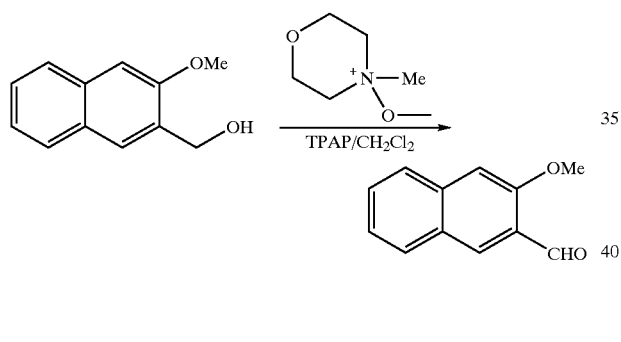

C. Preparation of 3-methoxy-2-naphthaldehyde. A solution of 2-hydroxymethyl-3-methoxynaphthalene (34.0 g, 0.181 mol) and 4-methylmorpholine N-oxide (23.1 g, 0.199 mol) in methylene chloride was cooled to 0° C. Tetrapropylammonium perruthenate (1.27 g, 3.62 mmol) was added and a reflux condenser was placed on top of the flask. The cooling bath was removed and within 15 min the mixture began to reflux. After cooling to room temperature the mixture was stirred for an additional 2 h. The mixture was filtered through silica gel (approximately 500 cm$^3$) that was then washed repeatedly with ether. The combined filtrates were concentrated in vacuo to provide 31.1 g (92%) of the title compound as a light tan solid. $^1$H NMR (CDCl$_3$) δ10.55 (s, 1H), 8.33 (s, 1H), 7.88 (d, J=8 Hz, 1H), 7.74 (d, J=8 Hz, 1H), 7.53 (t, J=8 Hz, 1H), 7.38 (t, J=8 Hz, 1H), 7.17 (s, 1H), 4.02 (s, 3H).

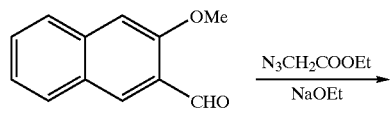

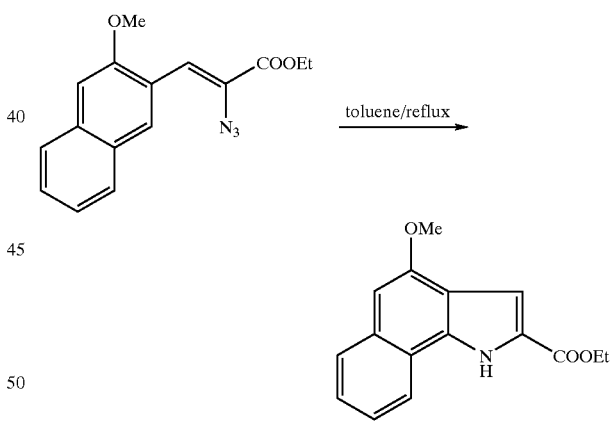

E. Preparation of 2-carboethoxy-4-methoxybenz[g]indole. A solution of 3-(3-methoxynaphth-2-yl)-2-azido-2-propenoic acid ethyl ester (12.0 g, 40.4 mmol) in toluene (300 mL) was refluxed for 3 h. The solution was cooled to room temperature and the resulting precipitate was collected via vacuum filtration and washed with hexane to provide 8.9 g (82%) of the title compound as a crystalline solid that may be recrystallized from ethyl acetate/hexane: mp 217–219° C. $^1$H NMR (DMSO-d$_6$) δ12.79 (bs, 1H, —NH), 8.64 (d, J=8 Hz, 1H), 7.82 (d, J=8 Hz, 1H), 7.45 (t, J=7 Hz, 1H), 7.37 (t, J=8 Hz, 1H), 7.22 (s, 1H), 6.88 (s, 1H), 4.37 (q, J=7 Hz, 2H), 3.98 (s, 3H), 1.35 (t, J=7 Hz, 3H); MS ES+ m/e 270 (p+1); IR (CHCl$_3$, cm$^{-1}$) 1689, 1517, 1313, 1264.

Anal. Calcd for $C_{16}H_{15}NO_3$: C, 71.36; H, 5.61; N, 5.20.

Found: C, 71.11; H, 5.50; N, 5.25.

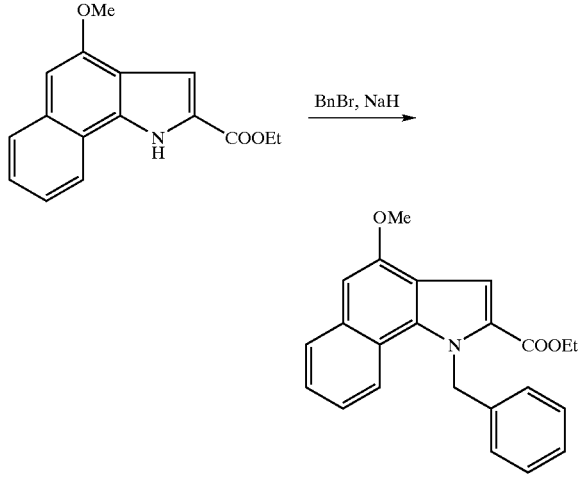

F. Preparation of 1-benzyl-2-carboethoxy-4-methoxybenz[g]indole. To a suspension of 60% sodium hydride in mineral oil (0.18 g, previously washed with hexanes in N,N-dimethylformamide (10 mL) was added 2-carboethoxy-4-methoxybenz[g]indole (1.00 g, 3.71 mmol) and benzyl bromide (0.51 mL, 4.3 mmol). The resulting mixture was stirred at room temperature for 18 h. Additional small portions of 60% sodium hydride suspension and benzyl bromide were added and the resulting mixture heated at ~40° C. for 4 h. Water was added and the resulting precipitate collected via vacuum filtration. Recrystallization of this material (ethyl acetate/hexane) provided 0.20 g of the title compound. The mother liquors were concentrated in vacuo. Chromatography (silica gel, 10% ethyl acetate/90% hexanes) of the residue provided an additional 0.41 g (46% total) of the title compound as a yellow solid: mp 171–173° C. $^1$H NMR (CDCl$_3$) δ8.07 (d, J=8.4 Hz, 1H), 7.79 (J=7.3 Hz, 1H), 7.72 (s, 1H), 7.39 (t, J=7.0 Hz, 1H), 7.15–7.35 (m, 4H), 7.11 (d, J=7.0 Hz, 2H), 6.78 (s, 1H), 6.34 (bs, 2H), 4.33 (q, J=7.3 Hz, 2H), 4.07 (s, 3H), 1.37 (t, J=7.3 Hz, 3H); MS ES+ m/e 360 (p+1); IR (CHCl$_3$, cm$^{-1}$) 1701, 1499, 1430.

Anal. Calcd for $C_{23}H_{21}NO_3$: C, 76.86; H, 5.89; N, 3.90.

Found: C, 76.66; H, 5.69; N, 3.94.

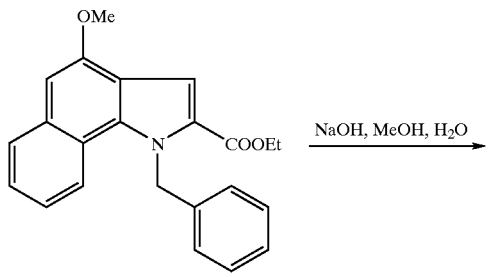

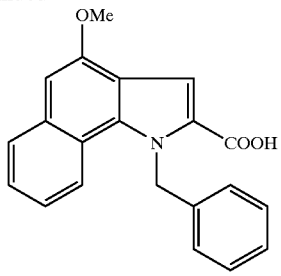

G. Preparation of 1-benzyl-2-carboxy-4-methoxybenz[g]indole. A solution of 1-benzyl-2-carboethoxy-4-methoxybenz[g]indole (0.81 g, 2.3 mmol) in water (20 mL), methanol (5 mL), and tetrahydrofuran (15 mL) was treated with sodium hydroxide (0.67 g, 17 mmol) at room temperature for 64 h. The mixture was filtered and concentrated in vacuo. The residue was slurried in water, acidified with concentrated hydrochloric acid, and the resulting precipitate collected via vacuum filtration. The solid was washed with water and dried to provide 0.47 g (63%) of the title compound as a beige solid: mp 257–259° C. (dec). $^1$H NMR (DMSO-d$_6$) δ12.92 (bs, 1H), 8.10 (d, J=8.4 Hz, 1H), 7.84 (d, J=7.0 Hz, 1H), 7.51 (s, 1H), 7.37 (t, J=7.7 Hz, 1H), 7.25 (m, 2H), 7.20 (m, 2H), 6.96 (d, J=8.8 Hz, 2H), 6.96 (s, 1H), 6.42 (bs, 2H), 4.01 (s, 3H); MS ES+ m/e 332 (p+1).

Anal. Calcd for $C_{21}H_{17}NO_3$: C, 76.12; H, 5.17; N, 4.23. Found: C, 75.80; H, 5.19; N, 4.06.

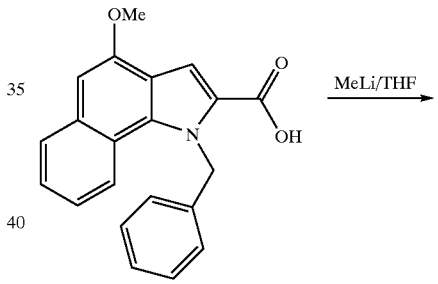

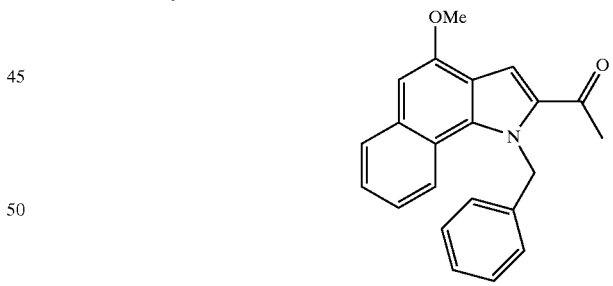

H. Preparation of 2-acetyl-1-benzyl-4-methoxybenz[g]indole. A solution of 1-benzyl-2-carboxy-4-methoxybenz[g]indole (3.00 g, 9.05 mmol) in anhydrous tetrahydrofuran (30 mL) was treated dropwise with 1.4 M methyllithium in ether (31.1 mL, 43.5 mmol) at room temperature. After stirring for 18 h, the mixture was poured into saturated ammonium chloride solution and acidified with aqueous hydrochloric acid. The mixture was extracted three times with ether. The combined ether extracts were washed once with water, once with saturated sodium chloride solution, dried (sodium sulfate), filtered, and concentrated in vacuo. Chromatography (silica gel, 10% ethyl acetate/90% hexane) of the residue provided 0.74 g (25%) of the title compound as a white crystalline solid: mp 189–191° C. $^1$H NMR (CDCl$_3$) δ8.09 (d, J=8 Hz, 1H), 7.77 (d, J=8 Hz, 1H), 7.67 (s, 1H), 7.38 (t, J=7 Hz, 1H), 7.30–7.15 (m, 4H), 7.07 (d, J=8 Hz, 2H), 6.78 (s, 1 H), 6.35 (bs, 2H), 4.08 (s, 3H), 2.63 (s, 3H); MS ES+ m/e 330 (p+1); IR (CHCl$_3$, cm$^{-1}$) 1657, 1429.

Anal. Calcd for C$_{22}$H$_{19}$NO$_2$: C, 80.22; H, 5.81; N, 4.25.

Found: C, 80.22; H, 5.77; N, 4.28.

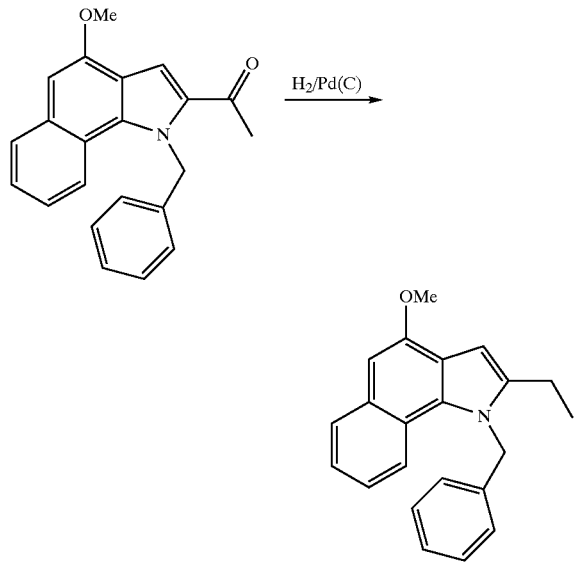

I. Preparation of 1-benzyl-2-ethyl-4-methoxybenz[g]indole. A mixture of 2-acetyl-1-benzyl-4-methoxybenz[g]indole (0.70 g, 2.1 mmol) and 10% palladium-on-carbon (300 mg) in 1:1 ethyl acetate/ethanol (50 mL) was hydrogenated at room temperature under 40 psi pressure for 18 h. Chloroform (3 mL) was added and the mixture further hydrogenated for 18 h. The mixture was filtered through Celite™ which was washed thoroughly with ethyl acetate. The combined washings were concentrated in vacuo to provide 0.47 g (70%) of the title compound as an off-white solid. $^1$H NMR (CDCl$_3$) δ7.95 (d, J=8 Hz, 1H), 7.79 (d, J=8 Hz, 1H), 7.25 (m, 4H), 7.15 (t, J=7 Hz, 1H), 7.05 (d, J=8 Hz, 2H), 6.82 (s, 1H), 6.67 (s, 1H), 5.78 (s, 2H), 4.08 (s, 3H), 2.76 (q, J=7 Hz, 2H), 1.37 (t, J=7 Hz, 3H); MS ES+ m/e 315 (p+1); IR (CHCl$_3$, cm$^{-1}$) 3008, 1531, 1470.

Anal. Calcd for C$_{22}$H$_{21}$NO: C, 83.78; H, 6.71; N, 4.44.

Found: C, 83.61; H, 6.54; N, 4.38.

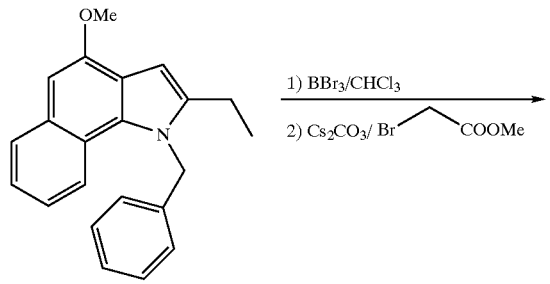

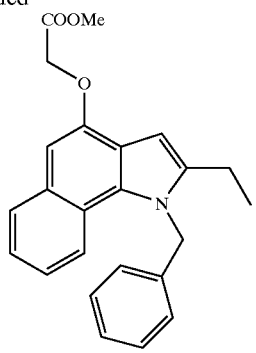

J. Preparation of 2-[(2-ethyl-1-benzyl-1H-benz[g]indol-4-yl)oxy]acetic acid methyl ester. A solution of 1-benzyl-2-ethyl-4-methoxybenz[g]indole (0.43 g, 1.4 mmol) in chloroform (8 mL) was cooled to 0° C. and treated with boron tribromide (0.36 mL, 3.8 mmol). The mixture was warmed to room temperature over 2 h, and poured into water. The mixture was extracted with fresh chloroform. The combined chloroform extracts were washed once with water, once with saturated sodium chloride solution, dried (sodium sulfate), filtered, and concentrated in vacuo to provide a highly colored solid. This material was added to a suspension of cesium carbonate (0.77 g, 2.4 mmol) in N,N-dimethylformamide (8 mL) and treated with methyl bromoacetate (0.23 mL, 2.4 mmol) at room temperature for 2 h. The mixture was diluted with water, and extracted twice with ethyl acetate. The combined ethyl acetate fractions were washed three times with water and once with saturated sodium chloride solution. The resulting solution was dried (sodium sulfate), filtered, and concentrated in vacuo to provide a red solid. Chromatography (silica gel, 20% ethyl acetate/80% hexane) provided 376 mg (74%) of the title compound as a white solid: mp 165–167° C. $^1$H NMR (CDCl$_3$) δ7.95 (d, J=8.4 Hz, 1H), 7.75 (d, J=8.1 Hz, 1H), 7.28 (m, 4H), 7.16 (t, J=7.0 Hz, 1H), 7.05 (d, 6.6 Hz, 2H), 6.74 (s, 1H), 6.69 (s, 1H), 5.77 (s, 2H), 4.91 (s, 2H), 3.85 (s, 3H), 2.76 (q, J=8.4 Hz, 2H), 1.38 (t, J=7.3 Hz, 3H); MS ES+ m/e 374 (p+1).

Anal. Calcd for C$_{24}$H$_{23}$NO$_3$: C, 77.19; H, 6.21; N, 3.75.

Found: C, 77.32; H, 6.02; N, 3.80.

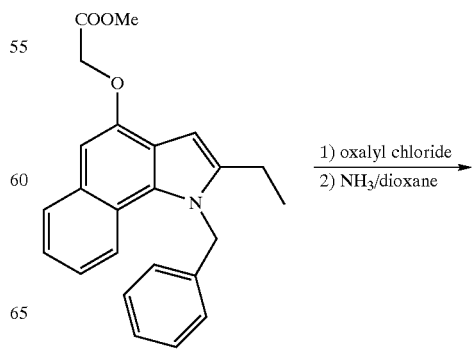

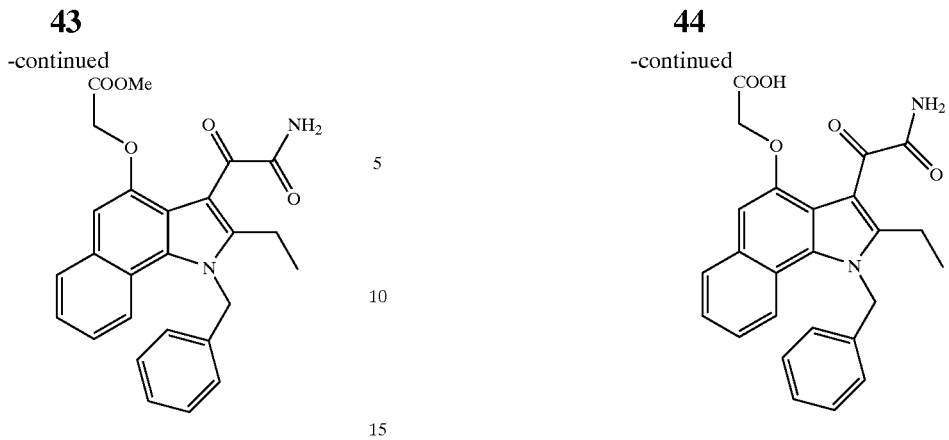

K. Preparation of 2-[[3-(2-amino-1,2-dioxoethyl)-2-ethyl-1-benzyl-1H-benz[g]indol-4-yl]oxy]acetic acid methyl ester hemihydrate. A solution of 2-[(2-ethyl-1-benzyl-1H-benz[g]indol-4-yl)oxy]acetic acid methyl ester (0.35 g, 0.94 mmol) in tetrahydrofuran (10 mL) was cooled to 0° C. and treated with oxalyl chloride (0.41 mL, 4.7 mmol). The mixture was stirred for 1 h, concentrated in vacuo, dissolved in a minimum of tetrahydrofuran, and treated at room temperature with 0.5 M ammonia in dioxane (20 mL). After stirring for 1 h, the mixture was concentrated in vacuo, dissolved in ethyl acetate, and washed once with water. The organic layer was dried, filtered, and concentrated in vacuo to provide crude product. Chromatography (silica gel, 65% ethyl acetate/35% hexane followed by 20% methanol/80% chloroform) provided 18 mg (4%) of the title product as a crystalline solid: mp 165–167° C.

$^1$H NMR (CDCl$_3$) δ7.90 (d, J=8.6 Hz, 1H), 7.74 (d, J=8.3 Hz, 1H), 7.28 (m, 4H), 7.16 (t, J=6.7 Hz, 1H), 7.09 (d, J=6.6 Hz, 2H), 6.79 (s, 1H), 6.65 (bs, 1H, —NH), 5.82 (s, 2H), 5.50 (bs, 1H, —NH), 4.83 (s, 2H), 3.79 (s, 3H), 2.92 (q, J=7.5 Hz, 2H), 1.22 (t, J=7.6 Hz, 3H); MS ES+ m/e 445 (p+1).

Anal. Calcd for C$_{26}$H$_{24}$N$_2$O$_5$. ½ H$_2$O: C, 68.86; H, 5.56; N, 6.18. Found: C, 69.09; H, 5.51; N, 6.14.

EXAMPLE 2

2-[[3-(2-Amino-1,2-dioxoethyl)-2-ethyl-1-benzyl-1H-benz[g]indol-4-yl]oxy]acetic acid

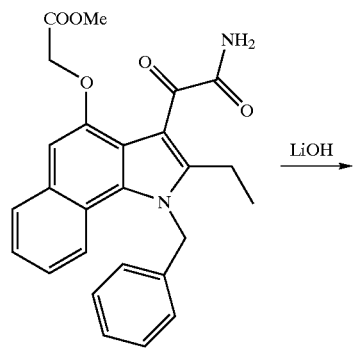

LiOH

Preparation of 2-[[3-(2-amino-1,2-dioxoethyl)-2-ethyl-1-benzyl-1H-benz[g]indol-4-yl]oxy]acetic acid. A mixture of 2-[[3-(2-amino-1,2-dioxoethyl)-2-ethyl-1-benzyl-1H-benz[g]indol-4-yl]oxy]acetic acid methyl ester hemihydrate (8 mg, 0.022 mmol) in 1 M aqueous lithium hydroxide solution (2 mL) and methanol (1 mL) was stirred at 40° C. for 2 h and at room temperature for 18 h. The mixture was concentrated in vacuo and acidified with aqueous hydrochloric acid. The resulting precipitate was collected via vacuum filtration, washed with water, and dried to provide 4.0 mg (53%) of the title product as a yellow solid. $^1$H NMR (DMSO-d$_6$) δ8.18 (bs, 1H, —NH), 8.03 (d, J=9 Hz, 1H), 7.81 (d, J=8 Hz, 1H), 7.48 (bs, 1H, —NH), 7.32 (m, 4H), 7.18 (t, J=7 Hz, 1H), 7.06 (d, J=7 Hz, 2H), 6.90 (s, 1H), 5.82 (s, 2H), 4.65 (s, 2H), 2.93 (q, J=8 Hz, 2H), 1.15 (t, J=8 Hz, 3H); TOF MS ES$^+$ exact mass calculated for C$_{25}$H$_{23}$N$_2$O$_5$ (p+1): m/z= 431.1607. Found: 431.1587.

Alternate synthesis of intermediate 1-benzyl-2-ethyl-4-methoxybenz[g]indole

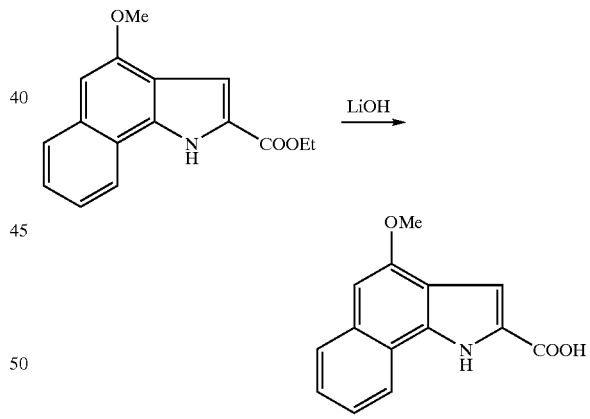

A. Preparation of 2-carboxy-4-methoxybenz[g]indole. A mixture of 2-carboethoxy-4-methoxybenz[g]indole (11.4 g, 42.3 mmol), methanol (100 mL), and 1 M aqueous lithium hydroxide solution (130 mL) was heated at 50° C. for 18 h, then at reflux for 4 h. While still warm the mixture was filtered and the filtrate allowed to stand at room temperature for 18 h. The slurry was acidified with aqueous hydrochloric acid and the resulting precipitate was collected via vacuum filtration to provide 8.7 g (96%) of the title product as a white solid that may be recrystallized from methanol/water: mp 262–264° C. (dec). $^1$H NMR (DMSO-d$_6$) δ12.89 (bs, 1H), 12.73 (bs, 1H), 8.67 (d, J=8 Hz, 1H), 7.80 (d, J=8 Hz, 1H), 7.43 (t, J=8 Hz, 12H), 7.37 (t, J=8 Hz, 1H), 7.22 (d, J=1 Hz, 1H), 6.85 (s, 1H), 3.97 (s, 3H); $^{13}$C NMR (DMSO-d$_6$)

δ162.46, 152.37, 134.09, 132.92, 127.20, 126.58, 125.55, 123.25, 122.17, 118.68, 117.26, 106.24, 97.21, 55.08; MS ES+ m/e 242 (p+1); IR (KBr, cm$^{-1}$) 3453, 1665, 1527, 1279.

Anal. Calcd for $C_{14}H_{11}NO_3$: C, 69.70; H, 4.60; N, 5.81. Found: C, 69.53; H, 4.70; N, 5.86.

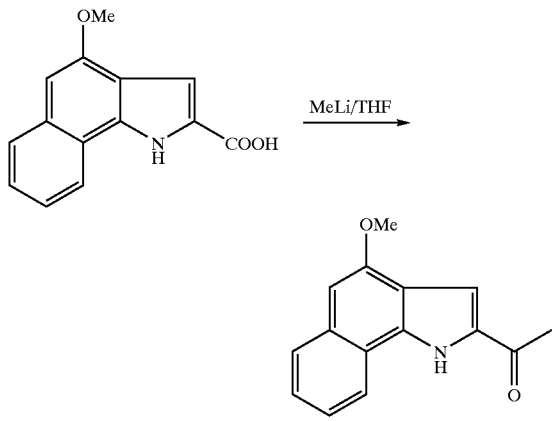

B. Preparation of 2-acetyl-4-methoxybenz[g]indole. A solution of 2-carboxy-4-methoxybenz[g]indole (0.24 g, 1.0 mmol) in tetrahydrofuran (3 mL) was treated with 1.4 M methyllithium in ether (5.0 mL, 7.0 mmol) at room temperature. After stirring for 1 h, an additional portion of 1.4 M methyllithium in ether (1.4 mL, 2.0 mmol) was added and the mixture stirred at room temperature for 2 h. The reaction was quenched with water and the mixture poured into saturated aqueous ammonium chloride solution. The mixture was extracted with ether and the organic layer washed once with water, once with saturated sodium chloride solution, dried (sodium sulfate), and filtered through a pad of silica gel. The pad was thoroughly washed with 20% ethyl acetate/80% hexane and the filtrate concentrated in vacuo. Recrystallization (ethyl acetate) of the residue provided 0.17 g (71%) of the title product as yellow crystals: mp 258–260° C. $^1$H NMR (DMSO-d$_6$) δ8.68 (d, J=8 Hz, 1H), 7.80 (d, J=8 Hz, 1H), 7.47 (s, 1H), 7.44 (t, J=8 Hz, 1H), 7.37 (t, J=8 Hz, 1H), 6.85 (s, 1H), 3.98 (s, 3H), 2.57 (s, 3H); $^{13}$C NMR (DMSO-d$_6$) δ189.13, 152.57, 134.95, 134.29, 133.50, 127.25, 126.01, 123.33, 122.27, 118.63, 117.45, 108.60, 97.37, 55.08, 26.02; MS ES+ m/e 240 (p+1); IR (KBr, cm$^{-1}$) 3279, 1655, 1275, 1190, 820.

Anal. Calcd for $C_{15}H_{13}NO_2$: C, 75.30; H, 5.48; N, 5.85. Found: C, 75.06; H, 5.52; N, 5.87.

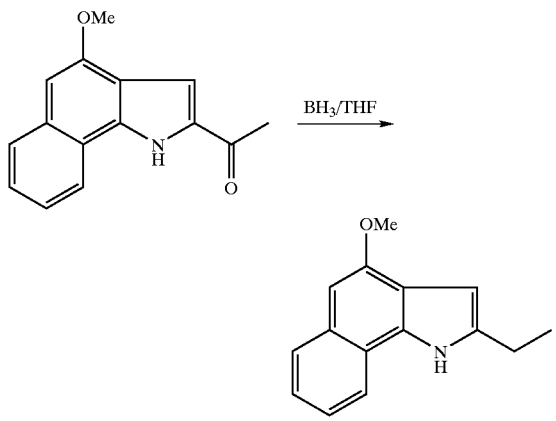

C. Preparation of 2-ethyl-4-methoxybenz[g]indole. A solution of 2-acetyl-4-methoxybenz[g]indole (6.15 g, 25.7 mmol) in tetrahydrofuran (50 mL) was treated with 1 M borane-tetrahydrofuran complex in tetrahydrofuran (75 mL, 75 mmol) at room temperature for 18 h. The reaction was carefully quenched with 1 N aqueous hydrochloric acid solution. The mixture was diluted with water and extracted with ether. The ether extract was washed once with water and once with saturated sodium chloride solution, dried (sodium sulfate), filtered, and concentrated in vacuo. Chromatography (silica gel, 10% ethyl acetate/90% hexane) of the residue provided 1.97 g (34%) of the title product as a white solid: mp 131–133° C. $^1$H NMR (CDCl$_3$) δ8.59 (bs, 1H, —NH), 7.85 (m, 2H), 7.38 (m, 2H), 6.82 (s, 1H), 6.54 (s, 1H), 4.07 (s, 3H), 2.87 (q, J=8 Hz, 2H), 1.42 (t, J=8 Hz, 3H); $^{13}$C NMR (CDCl$_3$) δ152.73, 138.94, 131.53, 131.25, 127.67, 123.86, 122.95, 118.97, 118.17, 97.65, 96.80, 55.23, 21.46, 13.51; MS ES+ m/e 226 (p+1); IR (CHCl$_3$, cm$^{-1}$) 3470, 3009, 1538, 1401.

Anal. Calcd for $C_{15}H_{15}NO$: C, 79.97; H, 6.71; N, 6.22.

Found: C, 79.82; H, 6.42; N, 6.19.

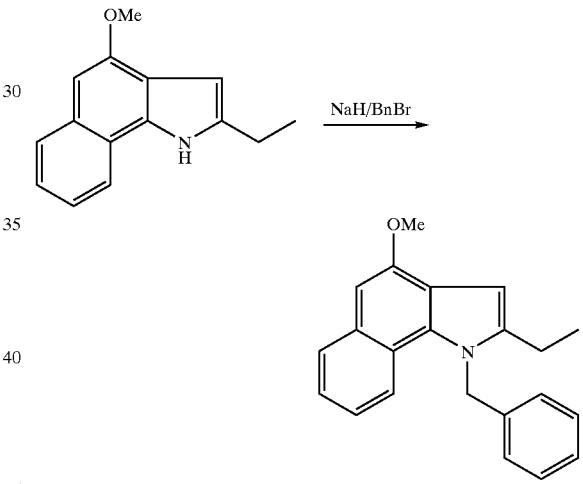

D. Preparation of 1-benzyl-2-ethyl-4-methoxybenz[g] indole. A solution of 2-ethyl-4-methoxybenz[g]indole (1.00 g, 4.44 mmol) in N,N-dimethylformamide (10 mL) was treated with 60% sodium hydride dispersion (0.21 g) at room temperature for 10 min. Benzyl bromide (0.068 mL, 5.2 mmol) was added and the mixture was stirred at room temperature for 16 h, at which point additional portions of sodium hydride (0.10 mg) and benzyl bromide (0.034 mL) were added. After stirring for 2 h, the mixture was diluted with water and extracted with ethyl acetate. The ethyl acetate layer was dried (sodium sulfate), filtered, and concentrated in vacuo.

Chromatography (silica gel, 20% toluene/80% hexane) of the residue provided 530 mg (38%) of the title product as a crystalline solid (identical to 1-benzyl-2-ethyl-4-methoxybenz[g]indole prepared as described above) which may be recrystallized from hexane/ethyl acetate: mp 165–167° C.

EXAMPLE 3

2-[[3-(2-amino-1,2-dioxoethyl)-2-methyl-1-cyclohexylmethyl-1H-benz[g]indol-4-yl]oxy]acetic acid methyl ester

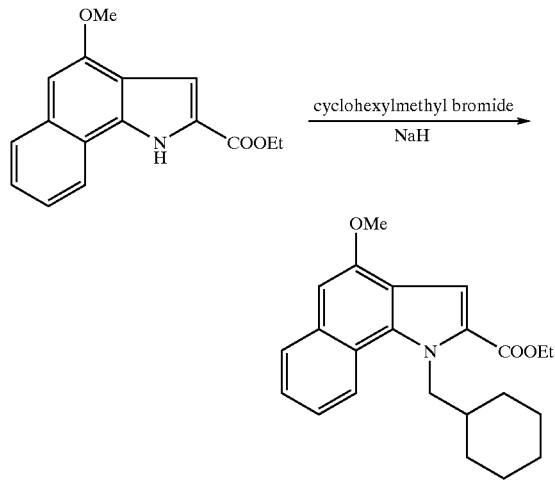

A. Preparation of 1-cyclohexylmethyl-2-carboethoxy-4-methoxybenz[g]indole. A solution of 2-carboethoxy-4-methoxyindole (8.94 g, 33.2 mmol) in N,N-dimethylformamide (200 mL) was treated with a 60% dispersion of sodium hydride in mineral oil (1.60 g, 40 mmol). After stirring for 30 min, bromomethylcyclohexane (5.5 mL, 39 mmol) was added and the mixture allowed to stir at room temperature for 5 days. Additional portions of 60% sodium hydride dispersion and bromomethylcyclohexane (approximately 0.2 equivalents) were added and the resulting mixture stirred for 2 days. Water (600 mL) was added and the resulting white precipitate was collected via vacuum filtration, washed once with water, and dried to provide 10.9 g (90%) of the title compound as an off-white solid. An analytical sample was prepared by recrystallization from hexanes: mp 148–150° C. $^1$H NMR (CDCl$_3$) δ8.26 (d, J=9.5 Hz, 1H), 7.82 (m, 1H), 7.56 (s, 1H), 7.43 (m, 2H), 6.75 (s, 1H), 5.08 (bs, 2H), 4.36 (q, J=7.3 Hz, 2H), 4.04 (s, 3H), 1.95 (bs, 1H), 1.60 (m, 5H), 1.41 (t, J=7.3 Hz, 3H), 1.10 (m, 5H); MS ES+ m/e 366 (p+1); IR (KBr, cm$^{-1}$) 2928, 1707, 1233.

Anal. Calcd for C$_{23}$H$_{27}$NO$_3$: C, 75.59; H, 7.45; N, 3.83.

Found: C, 75.23; H, 7.41; N, 3.99.

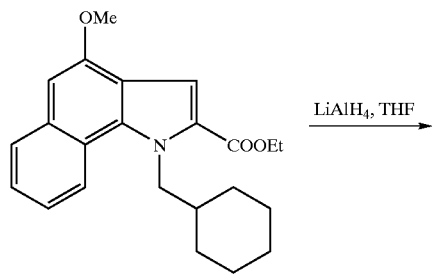

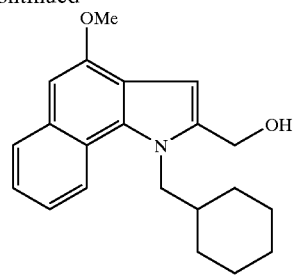

B. Preparation of 1-cyclohexylmethyl-2-hydroxymethyl-4-methoxybenz[g]indole. A solution of 1-cyclohexylmethyl-2-carboethoxy-4-methoxybenz[g]indole (9.80 g, 26.8 mmol) in tetrahydrofuran (250 mL) was treated carefully with lithium aluminum hydride (1.08 g, 28.5 mmol) at room temperature. After stirring for 2 h, an excess of sodium sulfate decahydrate was added and the resulting mixture filtered. The filtrate was further dried (sodium sulfate), filtered, and concentrated in vacuo to provide 8.2 g (94%) of the title compound as a white solid. An analytical sample was recrystallized from ethyl acetate/hexanes: mp 161–163° C.

$^1$H NMR (CDCl$_3$) δ8.12 (d, J=9.1 Hz, 1H), 7.76 (m, 1H), 7.31 (m, 3H), 6.72 (s, 1H), 4.43 (m, 4H), 3.97 (s, 3H), 1.93 (bs, 1H), 1.54 (m, 6H), 1.03 (m, 5H); MS ES+ m/e 324 (p+1); IR (KBr, cm$^{-1}$) 3417 (b), 2921, 1430, 1002.

Anal. Calcd for C$_{21}$H$_{25}$NO$_2$: C, 77.98; H, 7.79; N, 4.33. Found: C, 77.73; H, 7.72; N, 4.38.

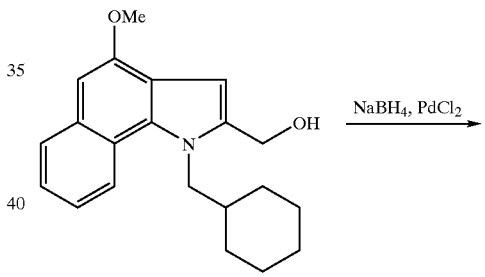

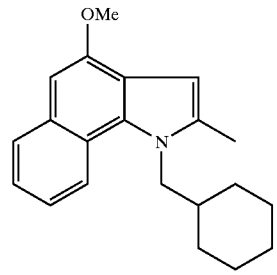

C. Preparation of 1-cyclohexylmethyl-2-methyl-4-methoxybenz[g]indole. A solution of 1-cyclohexylmethyl-2-hydroxymethyl-4-methoxybenz[g]indole (0.420 g, 1.30 mmol) and methanol (4 mL) in tetrahydrofuran (45 mL) was treated with palladium(II) chloride (0.404 g, 228 mmol) at room temperature. Sodium borohydride (0.15 g, 3.9 mmol) was added in portions over 10 min. The resulting mixture was stirred for 1 h then treated with water (0.5 mL). The mixture was filtered through a pad of silica gel and the filtrate concentrated in vacuo. The residue was dissolved in ethyl acetate and ether and washed once with water and once with saturated sodium chloride solution. The organic layer was dried (sodium sulfate), filtered, and concentrated in vacuo to provide 0.33 g (82%) of the title compound as an off-white solid. An analytical sample was recrystallized from hexanes: mp 138–141° C. $^1$H NMR (CDCl$_3$) δ8.11 (d, J=7.7 Hz, 1H), 7.82 (d, J=7.7 Hz, 1H), 7.37 (t, J=7.7 Hz, 1H), 7.33 (t, J=7.0 Hz, 1H), 6.77 (s, 1H), 6.49 (s, 1H), 4.27 (bd, J=7.3 Hz, 2H), 4.03 (s, 3H), 2.48 (s, 3H), 2.06 (bs, 1H), 1.66 (m, 5H), 1.10 (m, 5H); MS ES+ m/e 308 (p+1); IR (KBr, cm$^{-1}$) 2918, 1529, 1232.

Anal. Calcd for C$_{21}$H$_{25}$NO: C, 82.04; H, 8.20; N, 4.56.

Found: C, 81.52; H, 8.38; N, 4.56.

the residue provided 0.23 g (42%) of the title compound as a white fibrous solid: mp 156–158° C. $^1$H NMR (CDCl$_3$) δ8.11 (d, J=8.4 Hz, 1H), 7.79 (d, J=8.1 Hz, 1H), 7.42 (t, J=6.6 Hz, 1H), 7.33 (t, J=7.0 Hz, 1H), 6.66 (s, 1H), 6.58 (s, 1H), 4.87 (s, 2H), 4.27 (d, J=7.3 Hz, 2H), 3.82 (s, 3H), 2.49 (s, 3H), 2.05 (bs, 1H), 1.68 (m, 5H), 1.12 (m, 5H); MS ES+ m/e 366 (p+1); IR (KBr, cm$^{-1}$) 2928, 1757, 1210.

Anal. Calcd for C$_{23}$H$_{27}$NO$_3$: C, 75.59; H, 7.45; N, 3.83.

Found: C, 75.49; H, 7.56; N, 3.60.

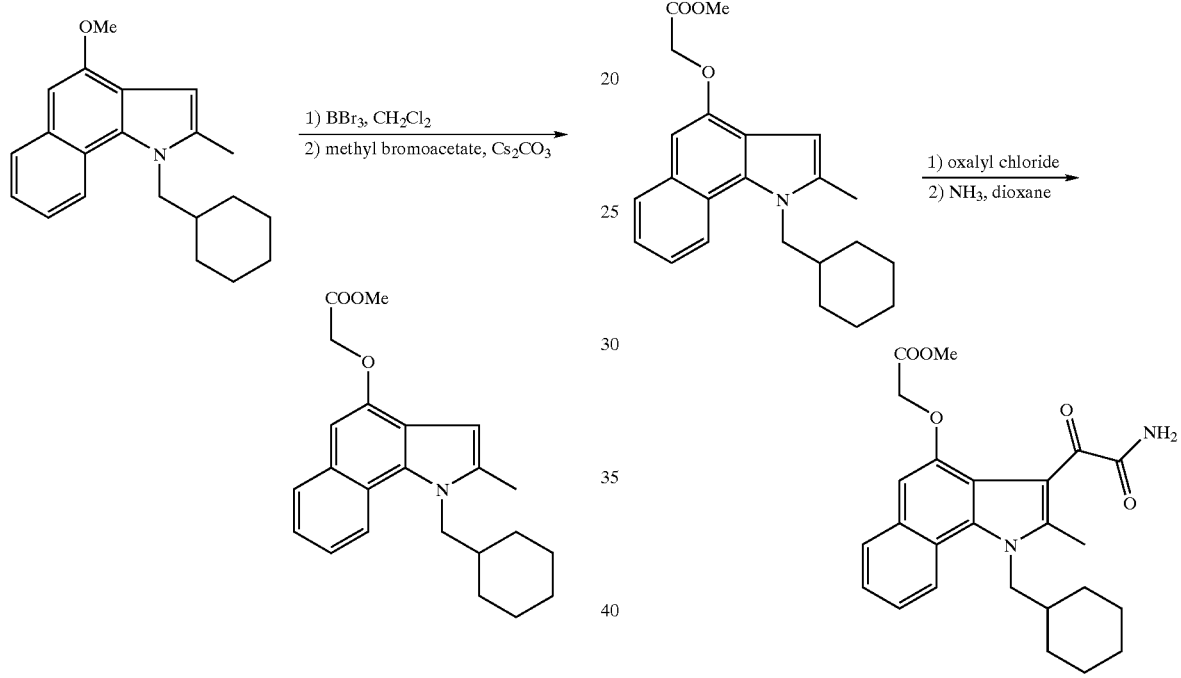

D. Preparation of 2-[(1-cyclohexylmethyl-2-methyl-1H-benz[g]indol-4-yl)oxy]acetic acid methyl ester. A solution of 1-cyclohexylmethyl-2-methyl-4-methoxybenz[g]indole (0.46 g, 1.5 mmol) in methylene chloride (14 mL) was cooled to 0° C. and treated with boron tribromide (0.35 mL, 3.7 mmol) in portions over 5 min. The mixture was allowed to warm to room temperature and stirred for 1 h. The mixture was poured onto ice and water and the resulting solution extracted with chloroform. The organic layer was washed once with water, once with dilute sodium bicarbonate solution, once with saturated sodium chloride solution, dried (sodium sulfate), filtered, and concentrated in vacuo. The residue was dissolved in N,N-dimethylformamide (10 mL) and treated with methyl bromoacetate (0.17 mL, 1.8 mmol) and cesium carbonate (0.64 g, 1.8 mmol) at room temperature with stirring for 29 h. The mixture was diluted with water and extracted three times with ethyl acetate. The combined ethyl acetate fractions were washed once with water, once with saturated sodium chloride solution, dried (sodium sulfate), filtered, and concentrated in vacuo. Chromatography (silica gel, 10% ethyl acetate/90% hexanes) of E. Preparation of 2-[[3-(2-amino-1,2-dioxoethyl)-1-cyclohexylmethyl-2-methyl-1H-benz[g]indol-4-yl]oxy] acetic acid methyl ester. A solution of 2-[(1-cyclohexylmethyl-2-methyl-1H-benz[g]indol-4-yl)oxy] acetic acid methyl ester (0.130 g, 0.356 mmol) in methylene chloride (5.0 mL) was treated with oxalyl chloride (0.16 mL, 1.8 mmol) at 0° C. After stirring for 1 h, the mixture was concentrated in vacuo, azeotroped twice with methylene chloride, dissolved in methylene chloride (5.0 mL), and treated with a solution of 0.5 M ammonia in dioxane (8 mL). The mixture was stirred for 20 min and concentrated in vacuo. Recrystallization of the residue (ethyl acetate) provided 94 mg (61%) of the title compound as a white solid: mp 197–199° C. $^1$H NMR (CDCl$_3$) δ8.12 (d, J=7.7 Hz, 1H), 7.80 (d, J=7.3 Hz, 1H), 7.42 (t, J=7.3 Hz, 1H), 7.39 (t, J=7.0 Hz, 1H), 6.79 (s, 1H), 6.67 (bs, 1H), 5.47 (bs, 1H), 4.81 (s, 2H), 4.34 (d, J=6.6 Hz, 2H), 3.79 (s, 3H), 2.61 (s, 3H), 2.05 (bs, 1H), 1.72 (m, 5H), 1.13 (m, 5H); MS ES+ m/e 437 (p+1); IR (KBr, cm$^{-1}$) 3155, 1730, 1643, 1406.

EXAMPLE 4

2-[[3-(2-Amino-1,2-dioxoethyl)-2-methyl-1-cyclohexylmethyl-1H-benz[g]indol-4-yl]oxy]acetic acid

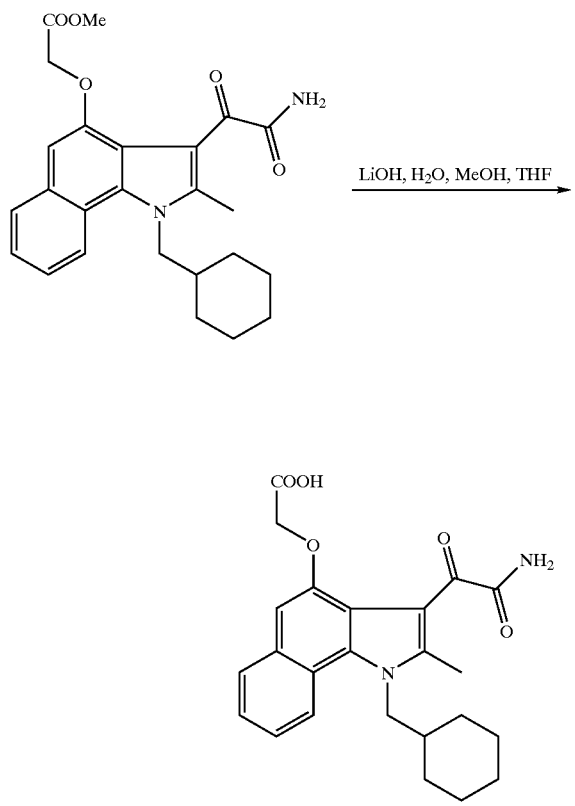

Preparation of 2-[[3-(2-amino-1,2-dioxoethyl)-1-cyclohexylmethyl-2-methyl-1H-benz[g]indol-4-yl]oxy] acetic acid. To a solution of 2-[[3-(2-amino-1,2-dioxoethyl)-1-cyclohexylmethyl-2-methyl-1H-benz[g]indol-4-yl]oxy] acetic acid methyl ester (0.042 g, 0.096 mmol) in 60% tetrahydrofuran/40% methanol (5 mL) was added 1 M lithium hydroxide solution (3 mL). The resulting mixture was stirred at room temperature for 28 h. The mixture was warmed briefly, diluted with water, and acidified with concentrated hydrochloric acid. The resulting yellow precipitate was collected via vacuum filtration and air-dried to provide 0.022 g (54%) of the title compound. $^1$H NMR (DMSO-$d_6$) δ13.00 (bs, 1H), 8.22 (d, J=8.4 Hz, 1H), 7.85 (d, J=7.3 Hz, 1H), 7.73 (bs, 1H), 7.48 (t, J=7.0 Hz, 1H), 7.45 (bs, 1H), 7.39 (t, J=7.0 Hz, 1H), 6.91 (s, 1H), 4.76 (s, 2H), 4.45 (bs, 2H), 2.55 (s, 3H), 1.90 (bs, 1H), 1.60 (m, 5H), 1.10 (m, 5H).

TOF MS ES+ exact mass calculated for $C_{24}H_{27}N_2O_5$ (p+1): m/z=423.1920. Found: 423.1949.

EXAMPLE 5

2-[[3-(2-Amino-1,2-dioxoethyl)-2-methyl-1-[3-(4-fluorophenyl)benzyl]-1H-benz[g]indol-4-yl]oxy] acetic acid methyl ester

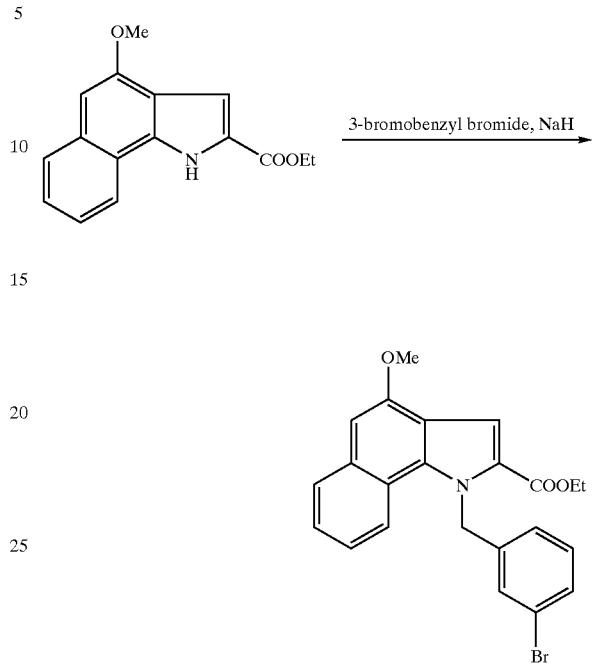

A. Preparation of 1-(3-bromobenzyl)-2-carboethoxy-4-methoxybenz[g]indole. To a slurry of 60% sodium hydride dispersion in mineral oil (3.27 g) in N,N-dimethylformamide (200 mL) was added 2-carboethoxy-4-methoxybenz[g]indole (14.4 g, 53.5 mmol). After stirring for 15 min a solution of 2-bromobenzyl bromide (16.0 g, 64.2 mmol) in N,N-dimethyformamide (20 mL) was added and the resulting mixture stirred for 18 h. The mixture was diluted with water and the resulting mixture extracted twice with ethyl acetate. The combined organic layers were washed once with water, once with saturated sodium chloride solution, dried (sodium sulfate), filtered, and concentrated in vacuo to provide 22.3 g (95%) of the title compound. An analytical sample was obtained by recrystallization (ethyl acetate/hexanes) to give off-white crystals: mp 184–186° C. $^1$H NMR (CDCl$_3$) δ7.95 (d, J=8.4 Hz, 1H), 7.78 (d, J=8.1 Hz, 1H), 7.68 (s, 1H), 7.35 (m, 2H), 7.27 (s, 1H), 7.20 (t, J=7.0 Hz, 1H), 7.13 (t, J=7.7 Hz, 1H), 6.96 (d, J=7.7 Hz, 1H), 6.76 (s, 1H), 6.25 (bs, 2H), 4.30 (q, J=7.0 Hz, 2H), 4.04 (s, 3H), 1.35 (t, J=7.3 Hz, 3H); MS ES+ m/e 438, 440; IR (CHCl$_3$, cm$^{-1}$) 1701, 1575, 1430.

Anal. Calcd for $C_{23}H_{20}BrNO_3$: C, 63.02; H, 4.60; N, 3.20. Found: C, 62.64; H, 4.56; N, 3.14.

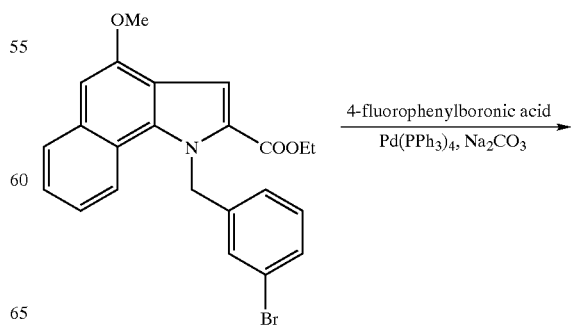

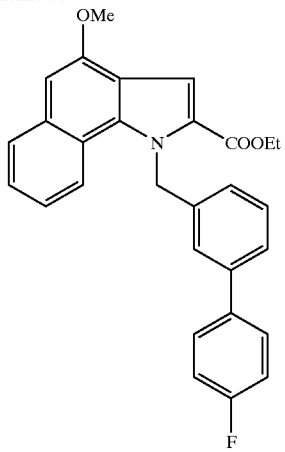

B. Preparation of 1-[3-(4-fluorophenyl)benzyl)]-2-carboethoxy-4-methoxybenz[g]indole. A mixture of 1-(3-bromobenzyl)-2-carboethoxy-4-methoxybenz[g]indole (10.4 g, 23.7 mmol), 4-fluorophenylboronic acid (4.97 g, 35.5 mmol), tetrakis(triphenylphosphine)palladium(0) (1.37 g, 1.19 mmol), and 2 M aqueous sodium carbonate solution (75 mL) in tetrahydrofuran (150 mL) was purged with nitrogen and heated at reflux for 48 h. The mixture was cooled to room temperature, poured into water, and the resulting solution extracted repeatedly with ethyl acetate. The combined organic layers were washed once with water, dried (sodium sulfate), filtered, and concentrated in vacuo. Chromatography (10% ethyl acetate/90% hexanes) provided 9.88 g (92%) of the title compound as a white solid. An analytical sample was obtained by recrystallization (ethyl acetate/hexanes): mp 169–171° C. $^1$H NMR (CDCl$_3$) δ8.07 (d, J=8.4 Hz, 1H), 7.77 (d, J=8.1 Hz, 1H), 7.69 (s, 1H), 7.25–7.45 (m, 6H), 7.29 (t, J=7.8 Hz, 1H), 7.05 (m, 3H), 6.76 (s, 1H), 6.36 (bs, 2H), 4.30 (q, J=7.0 Hz, 2H), 4.04 (s, 3H), 1.34 (t, J=7.3 Hz, 3H); MS ES+ m/e 454 (p+1); IR (KBr, cm$^{-1}$) 1705, 1185.

Anal. Calcd for C$_{29}$H$_{24}$FNO$_3$: C, 76.80; H, 5.33; N, 3.09.

Found: C, 76.91; H, 5.23; N, 2.97.

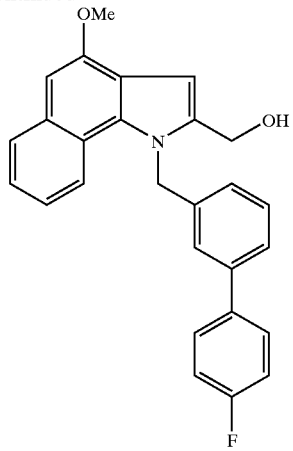

C. Preparation of 1-[3-(4-fluorophenyl)benzyl)]-2-hydroxymethyl-4-methoxybenz[g]indole. A solution of 1-[3-(4-fluorophenyl)benzyl)]-2-carboethoxy-4-methoxybenz[g]indole (9.80 g, 21.6 mmol) in tetrahydrofuran (200 mL) was carefully treated at room temperature with lithium aluminum hydride (0.82 g, 22 mmol) for 18 h. The mixture was treated with excess sodium sulfate decahydrate, filtered, and concentrated in vacuo to provide 7.14 g (80%) of the title compound as a beige solid. An analytical sample was recrystallized (ethyl acetate/hexanes) to provide beige crystals: mp 185–187° C. MS ES+ m/e 412 (p+1).

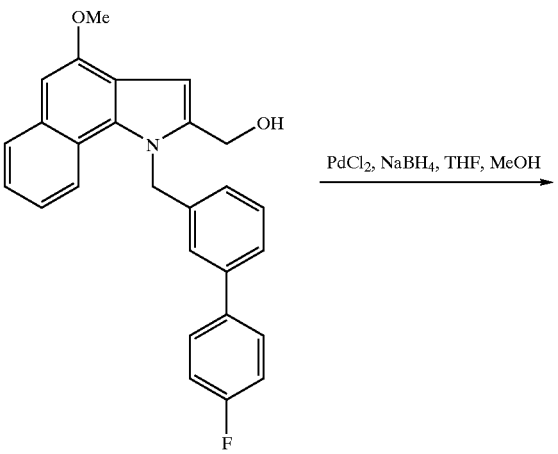

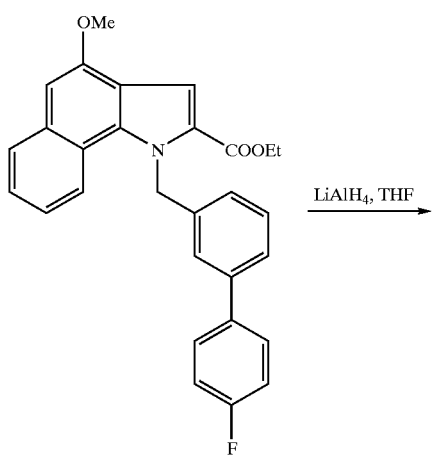

LiAlH$_4$, THF

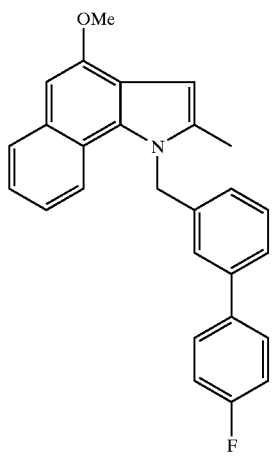

D. Preparation of 1-[3-(4-fluorophenyl)benzyl)]-2-methyl-4-methoxybenz[g]indole. A solution of 1-[3-(4-fluorophenyl)benzyl)]-2-hydroxymethyl-4-methoxybenz[g]indole (6.90 g, 16.8 mmol) in tetrahydrofuran (690 mL) and methanol (69 mL) was treated with palladium(II) chloride (5.20 g, 29.3 mmol) in one portion and sodium borohydride (1.91 g, 50.5 mmol) in portions over 30 min. After stirring for 2 h, water (5 mL) was added and the resulting mixture filtered through a pad of Celite™. The filtrate was concentrated in vacuo and the residue slurried in hot methanol. The resulting solids were collected via vacuum filtration. The filtrate was concentrated in vacuo to provide additional precipitate that was collected via vacuum filtration. The total yield of the title compound was 3.4 g (52%) as a light blue solid: mp 138° C. (dec). $^1$H NMR (DMSO-$d_6$) δ8.09 (d, J=8.4 Hz, 1H), 7.80 (d, J=7.7 Hz, 1H), 7.57 (m, 2H), 7.50 (d, J=7.7 Hz, 1H), 7.39 (s, 1H), 7.35 (t, J=8.1 Hz, 1H), 7.27 (m, 3H), 7.16 (t, J=7.3 Hz, 1H), 6.90 (s, 1H), 6.84 (d, J=7.7 Hz, 1H), 6.57 (S, 1H), 5.90 (S, 2H), 3.98 (s, 3H), 2.47 (s, 3H); MS ES+ m/e 396 (p+1); IR (CHCl$_3$, cm$^{-1}$) 3009, 1515, 1310.

Anal. Calcd for $C_{27}H_{22}FNO$: C, 82.00; H, 5.61; N, 3.54. Found: C, 82.03; H, 5.65; N, 3.44.

boron tribromide (0.72 mL, 7.6 mmol). The mixture was allowed to warm to room temperature over 2 h, then poured into water. The organic layer was separated and the aqueous layer extracted with a fresh portion of methylene chloride. The combined organic layers were washed once with dilute aqueous sodium bicarbonate, once with water, dried (sodium sulfate), filtered, and concentrated in vacuo. This material was dissolved in N,N-dimethylformamide (18 mL) and treated with cesium carbonate (1.06 g, 3.00 mmol) and methyl bromoacetate (0.30 mL, 3.2 mmol) at room temperature for 17 h. The mixture was diluted with water and the resulting solution extracted twice with ethyl acetate. The combined organic layeres were washed once with water, once with saturated sodium chloride solution, filtered, and concentrated in vacuo. Chromatography (10% ethyl acetate/90% hexanes) provided 0.49 g (43%) of the title compound as a white solid: mp 157–159° C. $^1$H NMR (CDCl$_3$) δ7.99 (d, J=8.4 Hz, 1H), 7.76 (d, J=8.1 Hz, 1H), 7.40 (m, 3H), 7.34 (t, J=7.7 Hz, 1H), 7.26 (m, 2H), 7.18 (t, J=7.0 Hz, 1H), 7.07 (m, 2H), 7.00 (d, J=7.7 Hz, 1H), 6.73 (s, 1H), 6.69 (s, 1H), 5.80 (s, 2H), 4.90 (s, 2H), 3.84 (s, 3H), 2.47 (s, 3H); MS ES+ m/e 454 (p+1). IR (KBr, cm$^{-1}$) 1759, 1220, 1185.

Anal. Calcd for $C_{29}H_{24}FNO_3$: C, 76.80; H, 5.33; N, 3.09. Found: C, 76.20; H, 5.22; N, 3.21.

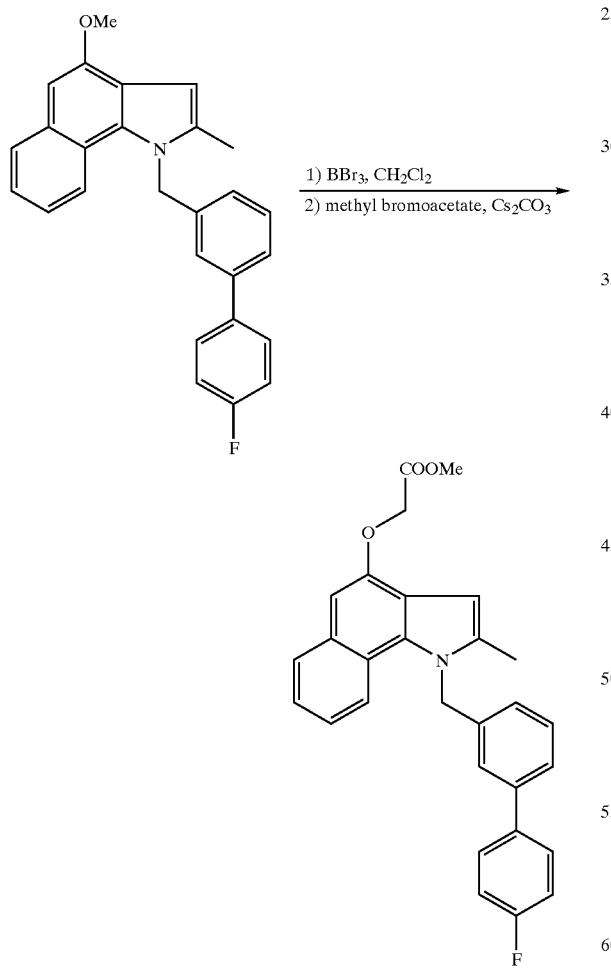

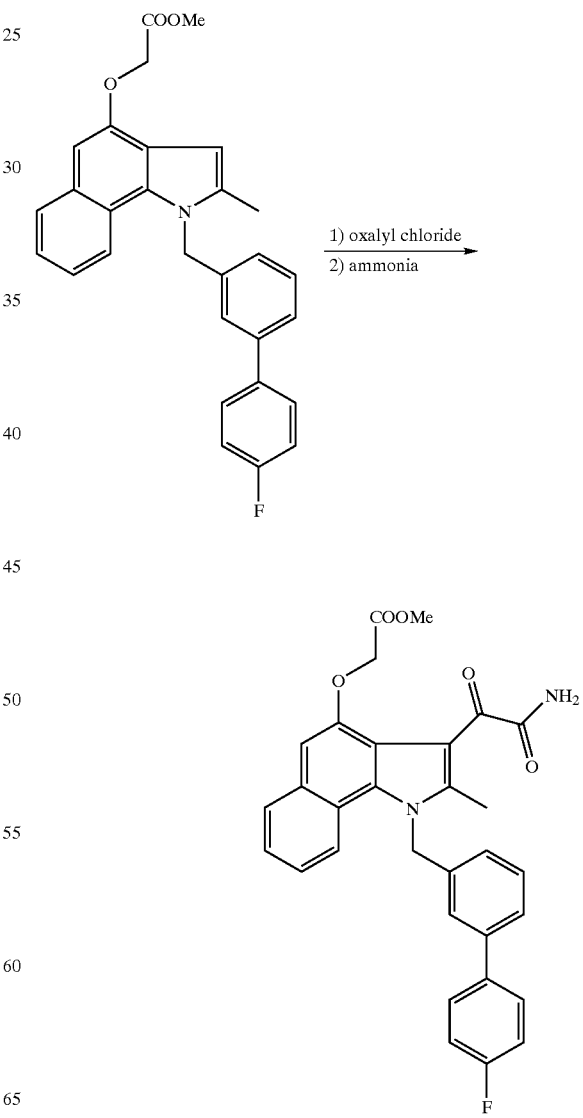

E. Preparation of 2-[[1-[3-(4-fluorophenylbenzyl)]-2-methyl-1H-benz[g]indol-4-yl]oxy]acetic acid methyl ester. A solution of 1-[3-(4-fluorophenyl)benzyl)]-2-methyl-4-methoxybenz[g]indole (1.00 g, 2.53 mmol) in methylene chloride (40 mL) was cooled in an ice bath and treated with F. Preparation of 2-[[3-(2-amino-1,2-dioxoethyl)-1-[3-(4-fluorophenylbenzyl)]-2-methyl-1H-benz[g]indol-4-yl]oxy] acetic acid methyl ester. A solution of 2-[[1-[3-(4-fluorophenylbenzyl)]-2-methyl-1H-benz[g]indol-4-yl]oxy] acetic acid methyl ester (279 mg, 0.615 mmol) in methylene chloride (10 mL) was cooled in an ice bath and treated with oxalyl chloride (0.30 mL, 3.4 mmol). The mixture was allowed to warm to room temperature over 2 h then concentrated in vacuo. Methylene chloride was added and the solution concentrated in vacuo, dissolved in methylene chloride, and treated with an excess of a solution of 0.5 M ammonia in dioxanes. The mixture was stirred for 1 h then concentrated in vacuo. The residue was slurried in hot ethyl acetate and filtered to provide 210 mg (65%) of the title compound as a light yellow solid.

TOF MS ES$^+$ exact mass calculated for $C_{31}H_{26}N_2O_5F$ (p+1): m/z=525.1826. Found: 525.1854.

EXAMPLE 6

2-[[3-(2-Amino-1,2-dioxoethyl)-2-methyl-1-[3-(4-fluorophenyl)benzyl]-1H-benz[g]indol-4-yl]oxy] acetic acid.

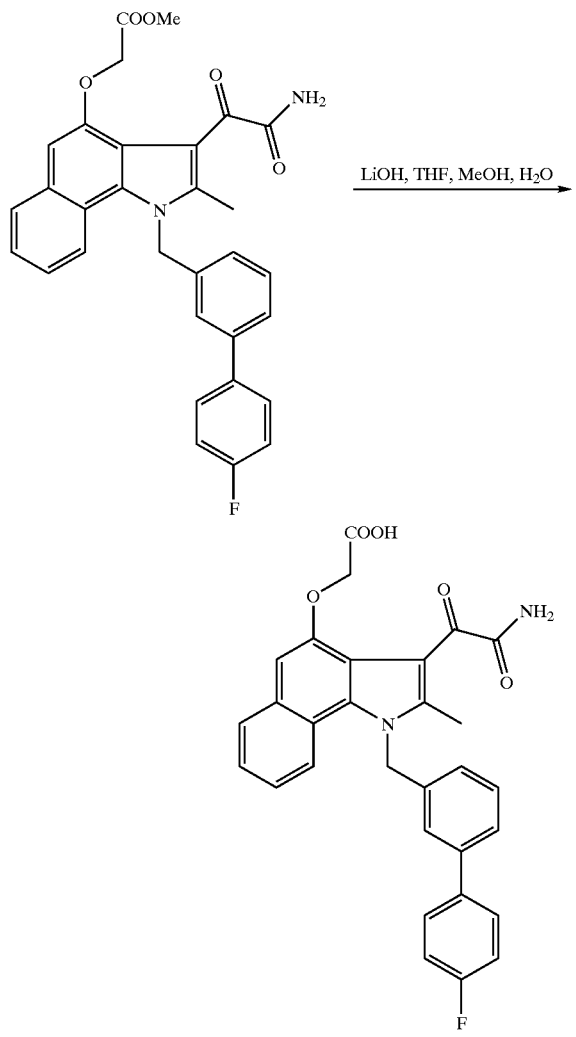

2-[[3-(2-amino-1,2-dioxoethyl)-1-[3-(4-fluorophenylbenzyl)]-2-methyl-1H-benz[g]indol-4-yl]oxy] acetic acid. A solution of 2-[[3-(2-amino-1,2-dioxoethyl)-1-[3-(4-fluorophenylbenzyl)]-2-methyl-1H-benz[g]indol-4-yl]oxy]acetic acid (150 mg, 0.29 mmol) in 1:1 tetrahydrofuran/methanol (8 mL) was treated with 1 M aqueous lithium hydroxide solution (5 mL) at room temperature for 18 h. The mixture was concentrated in vacuo, diluted with water, and treated with concentrated hydrochloric acid. The resulting precipitate was collected via vacuum filtration to provide 48 mg (33%) of the title compound as a brown solid: mp>160° C.

TOF MS ES$^+$ exact mass calculated for $C_{30}H_{24}N_2O_5F$ (p+1): m/z=511.1669. Found: 511.1699.

We claim:

1. A benz[g]indole compound represented by the formula (I), or a pharmaceutically acceptable salt, solvate or prodrug thereof;

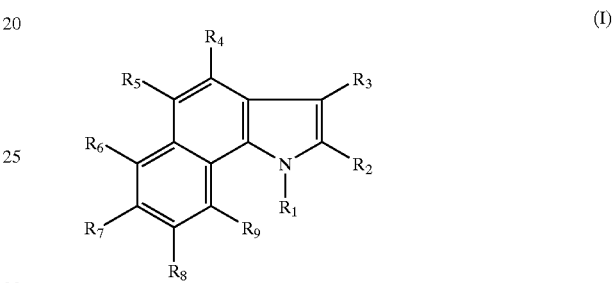

wherein;

$R_1$ is selected from group (a), (b), or (c)

wherein;

(a) is $C_2$–$C_{20}$ alkyl, $C_2$–$C_{20}$ haloalkyl, $C_2$–$C_{20}$ alkenyl, $C_2$–$C_{20}$ alkynyl, carbocyclic radical, or heterocyclic radical, or (b) is a member of (a) substituted with one or more groups independently selected from hydrogen, ($C_1$–$C_8$)alkyl, ($C_2$–$C_8$)alkenyl, ($C_2$–$C_8$) alkynyl, ($C_7$–$C_{12}$)aralkyl, ($C_7$–$C_{12}$)alkaryl, ($C_3$–$C_8$) cycloalkyl, ($C_{3-C8}$ cycloalkenyl, phenyl, toluyl, xylenyl, benzyl, biphenyl, ($C_1$–$C_8$)alkoxy, ($C_2$–$C_8$) alkenyloxy, ($C_2$–$C_8$)alkynyloxy, ($C_2$–$C_{12}$) alkoxyalkyl, and $C_{2-12}$)alkoxyalkyloxy;

(c) is the group -(L)-$R_{80}$; where, -(L)- is a divalent linking group of 1 to 12 atoms selected from carbon and hydrogen; and where $R_{80}$ is a group selected from (a) or (b);

$R_2$ is hydrogen, ($C_1$–$C_4$)alkyl, ($C_2$–$C_4$)alkenyl, —O—($C_1$–$C_3$ alkyl), —S—($C_1$–$C_3$alkyl), ($C_3$–$C_4$)cycloalkyl, —CF$_3$, halo, —NO$_2$, —CN, or —SO$_3$;

$R_3$ is -($L_3$)- Z, where -($L_3$)- is a divalent linker group selected from a bond or a divalent group selected from:

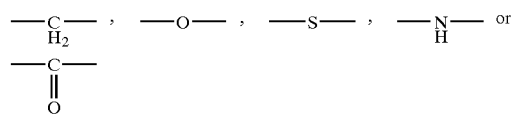

and Z is selected from an oxime amide or oxime thioamide group represented by the formulae,

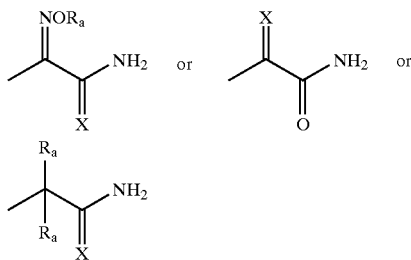

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, hydrogen, $CONH_2$, $CONHR^{4b}$ or —(La)-(acidic group) wherein $-(L_a)-$, is $OCH_2$;

or the group $-(L_h)$-(N-hydroxyfunctional amide group); wherein $-(L_h)-$, is $OCH_2$; and wherein a N-hydroxyfunctional amide group is represented by the formula:

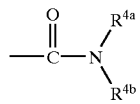

wherein $R^{4a}$ is selected from the group consisting of OH, $(C_1$–$C_6)$alkoxy, and aryloxy; and wherein $R^{4b}$ is hydrogen or an organic substituent selected from the group consisting of $(C_1$–$C_8)$alkyl, aryl, $(C_7$–$C_{14})$aralkyl, $(C_7$–$C_{14})$alkaryl, $(C_3$–$C_8)$cycloalkyl and $(C_1$–$C_8)$alkoxyalkyl;

$R_5$ is selected from hydrogen, $(C_1$–$C_8)$alkyl, $(C_2$–$C_8)$ alkenyl, $(C_2$–$C_8)$ alkynyl, $(C_7$–$C_{12})$aralkyl, $(C_7$–$C_{12})$ alkaryl, $(C_3$–$C_8)$cycloalkyl, $(C_3$–$C_8)$cycloalkenyl, phenyl, toluyl, xylenyl, benzyl, biphenyl, $(C_1$–$C_8)$ alkoxy, $(C_2$–$C_8)$alkenyloxy, $(C_2$–$C_8)$alkynyloxy, $(C_2$–$C_{12})$alkoxyalkyl, and $(C_2$–$C_{12})$alkoxyalkyloxy; and $R_6$, $R_7$, $R_8$, and $R_9$ are independently selected hydrogen, $(C_1$–$C_8)$alkyl, $(C_2$–$C_8)$alkenyl, $(C_2$–$C_8)$ alkynyl, $(C_7$–$C_{12})$aralkyl, $(C_7$–$C_{12})$alkaryl, $(C_3$–$C_8)$cycloalkyl, $(C_3$–$C_8)$cycloalkenyl, phenyl, toluyl, xylenyl, benzyl, biphenyl, $(C_1$–$C_8)$alkoxy, $(C_2$–$C_8)$alkenyloxy, $(C_2$–$C_8)$ alkynyloxy, $(C_2$–$C_{12})$alkoxyalkyl, and $(C_2$–$C_{12})$ alkoxyalkyloxy.

2. The compound of claim 1 wherein $R_2$, is hydrogen, $(C_1$–$C_4)$alkyl, $(C_2$–$C_4)$alkenyl, —O—$(C_1$–$C_3$ alkyl), —S—$(C_1$–$C_3$ alkyl) or $(C_3$–$C_4)$cycloalkyl.

3. The compound of claim 1 wherein for $R_3$, Z is the group represented by the formula;

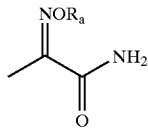

and the linking group $-(L_3)-$ is a bond; and $R_a$ is hydrogen, methyl, ethyl, propyl, isopropyl, phenyl or beazyl.

4. The compound of claim 1 wherein for $R_3$, Z is the group represented by the formula;

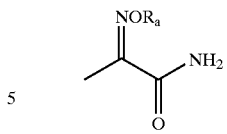

and the linking group $-(L_3)-$ is a bond; and $R_a$ is hydrogen.

5. The compound of claim 1 wherein for $R_3$, Z is the group represented by the formula;

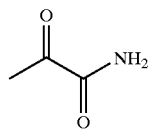

and the linking group $-(L_3)-$ is a bond.

6. The compound of claim 1 wherein for $R_3$, $R^a$ and $R^b$ are both hydrogen and X is oxygen and Z is the group represented by the formula;

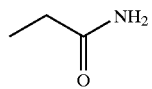

and the linking group $-(L_3)-$ is a bond.

7. The compound of claim 1 wherein $R_4$ is the group, $-(L_a)$-(acidic group) and wherein $-(L_a)-$ is $OCH_2$ and the (acidic group) is COOH.

8. A compound selected from the group consisting of:

2-[[3-(2-Amino-1,2-dioxoethyl)-2-ethyl-1-benzyl-1H-benz[g]indol-4-yl]oxy]acetic acid methyl ester hemihydrate;

2-[[3-(2-Amino-1,2-dioxoethyl)-2-ethyl-1-benzyl-1H-benz[g]indol-4-yl]oxy]acetic acid;

2-[[3-(2-amino-1,2-dioxoethyl)-2-methyl-1-cyclohexylmethyl-1H-benz[g]indol-4-yl]oxy]acetic acid methyl ester;

2-[[3-(2-Amino-1,2-dioxoethyl)-2-methyl-1-cyclohexylmethyl-1H-benz[g]indol-4-yl]oxy]acetic acid;

2-[[3-(2-Amino-1,2-dioxoethyl)-2-methyl-1-[3-(4-fluorophenyl)benzyl]-1H-benz[g]indol-4-yl]oxy]acetic acid methyl ester; and 2-[[3-(2-Amino-1,2-dioxoethyl)-2-methyl-1-[3-(4-fluorophenyl)benzyl]-1H-benz[g]indol-4-yl]oxy]acetic acid, or a pharmaceutically acceptable salt, prodrug or solvate thereof.

9. A benz[g]indole compound represented by the formulae (C1), (C2), (C3), (C4), (C5), or (C6):

(C1)
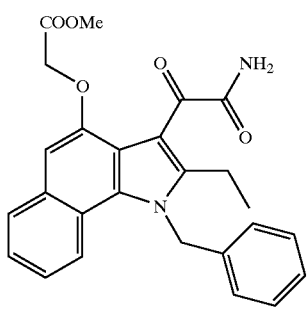

(C2)
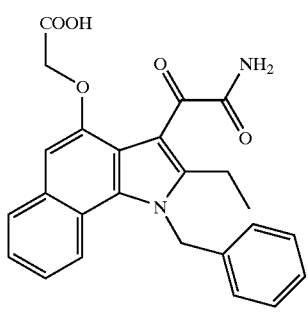

(C3)
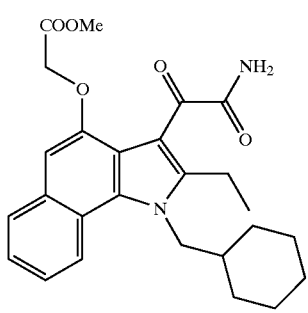

(C4)
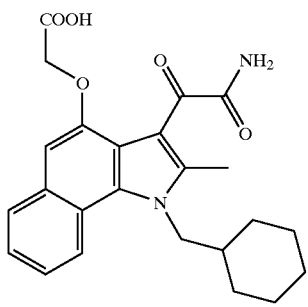

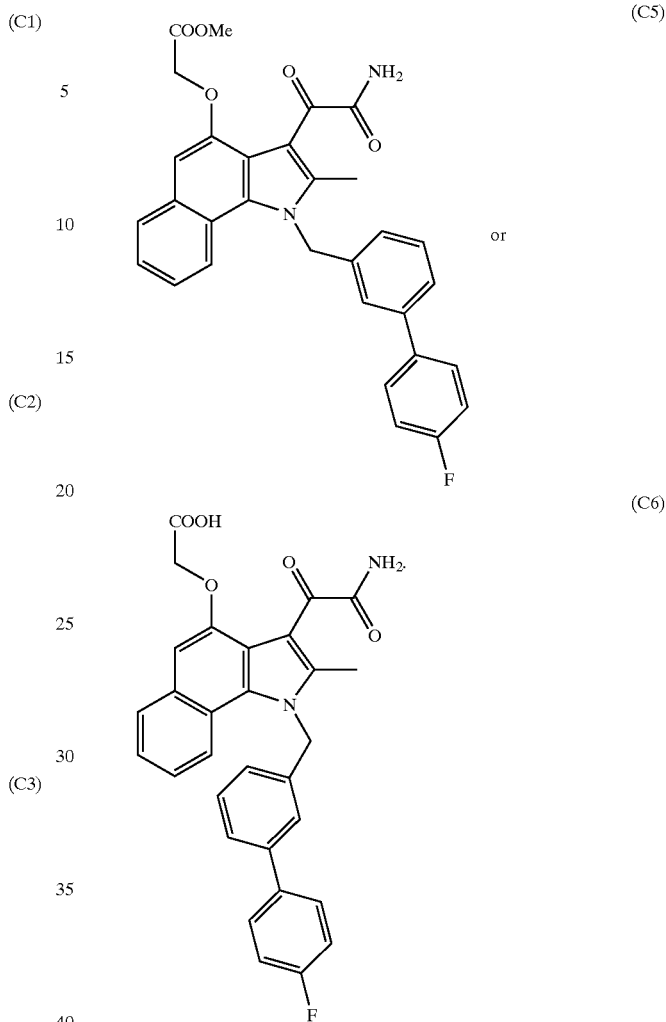

10. A pharmaceutical composition comprising a benz[g]indole compound of claim 1 together with a pharmaceutically acceptable carrier or diluent.

11. A method of inhibiting sPLA₂ mediated release of fatty acid comprising contacting sPLA₂ with a therapeutically effective amount of benz[g]indole compound of claim 1.

12. A method of treating a mammal to alleviate the pathological effects of sepsis; wherein the method comprises administering to said mammal a therapeutically effective amount of a benz[g]indole compound according to claim 1.

13. A pharmaceutical composition containing a therapeutically effective amount of the compound of claim 1 useful for the treatment and/or amelioration of sepsis.

* * * * *